United States Patent
White et al.

(10) Patent No.: US 6,416,553 B1
(45) Date of Patent: Jul. 9, 2002

(54) METHOD AND APPARATUS FOR PROVIDING A MODULAR ACETABULAR PROSTHESIS

(75) Inventors: John R. White, Winona Lake; Troy W. Hershberger, Warsaw, both of IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/537,505

(22) Filed: Mar. 29, 2000

Related U.S. Application Data

(60) Provisional application No. 60/127,023, filed on Mar. 31, 1999.

(51) Int. Cl.$^7$ .................................................. A61F 2/34
(52) U.S. Cl. .................................................. 623/22.38
(58) Field of Search ........................... 623/22.21, 22.24, 623/22.25, 22.28, 22.33, 22.34, 22.35, 22.36, 22.37, 22.38

(56) References Cited

U.S. PATENT DOCUMENTS

| | | |
|---|---|---|
| 2,947,308 A | 8/1960 | Gorman |
| 3,641,590 A | 2/1972 | Michele |
| 3,740,769 A | 6/1973 | Haboush |
| 3,896,504 A | 7/1975 | Fischer |
| 3,903,549 A | 9/1975 | Deyerle |
| 3,918,102 A | 11/1975 | Eichler |
| 4,245,360 A | 1/1981 | Brinckmann et al. |
| 4,437,193 A | 3/1984 | Oh |
| 4,623,353 A | 11/1986 | Buechel et al. |
| 4,792,337 A | 12/1988 | Muller |
| 4,871,368 A | 10/1989 | Wagner |
| 4,883,489 A | 11/1989 | Grundei et al. |
| 4,883,490 A | 11/1989 | Oh |
| 4,904,265 A | 2/1990 | MacCollum et al. |
| 4,919,672 A | 4/1990 | Millar et al. |
| 4,919,675 A | 4/1990 | Dietschi |
| 4,936,861 A | 6/1990 | Muller et al. |
| 4,955,919 A | 9/1990 | Pappas et al. |
| 4,959,072 A | 9/1990 | Morscher et al. |
| 4,961,748 A | 10/1990 | Frey et al. |
| 5,108,447 A | 4/1992 | Zeiler et al. |
| 5,156,625 A | 10/1992 | Marchetti et al. |
| 5,192,329 A | 3/1993 | Christie et al. |
| 5,226,917 A | 7/1993 | Schryver |
| 5,290,315 A | 3/1994 | DeCarlo, Jr. |
| 5,307,325 A | 4/1994 | Scheiber |
| 5,314,488 A | 5/1994 | Hayashi et al. |
| 5,314,490 A | 5/1994 | Wagner et al. |
| 5,326,367 A | 7/1994 | Robioneck |

(List continued on next page.)

FOREIGN PATENT DOCUMENTS

| | | |
|---|---|---|
| DE | 88 07 947.3 | 3/1994 |
| DE | 92 12 420.8 | 3/1994 |
| EP | 0 123 514 A1 | 10/1984 |
| EP | 0 242 719 A1 | 10/1987 |
| EP | 0 295 912 A1 | 12/1988 |
| EP | 0 402 810 A1 | 12/1990 |

(List continued on next page.)

*Primary Examiner*—David J. Isabella
(74) *Attorney, Agent, or Firm*—Harness, Dickey & Pierce, P.L.C.

(57) ABSTRACT

An acetabular prosthesis for implantation in an acetabulum includes an acetabular cup and a modular attachment component. The acetabular cup includes an outer surface operable to be received in the acetabulum and an inner surface operable to receive a bearing liner. The modular attachment component includes an attachment member and an engagement member. The attachment member is operable for use in attaching the modular attachment component to the acetabular cup and the engagement member is operable to engage a region of the acetabulum. The attachment member may nest within an anti-rotation counterbore or be slidably received within a channel of an attachment plate extending from the acetabular cup. The engagement member may be an elongated intramedullary blade, a flange or a hook.

26 Claims, 16 Drawing Sheets

U.S. PATENT DOCUMENTS

| | | |
|---|---|---|
| 5,326,368 A | 7/1994 | Collazo |
| 5,370,703 A | 12/1994 | Willert et al. |
| 5,370,704 A | 12/1994 | DeCarlo, Jr. |
| 5,425,778 A | 6/1995 | Zichner et al. |
| 5,487,743 A | 1/1996 | Laurain et al. |
| 5,507,819 A | 4/1996 | Wolf |
| 5,507,828 A | 4/1996 | Maumy et al. |
| 5,507,833 A | 4/1996 | Bohn |
| 5,549,691 A | 8/1996 | Harwin |
| 5,549,697 A | 8/1996 | Caldarise |
| 5,584,880 A | 12/1996 | Martinez |
| 5,609,646 A | 3/1997 | Field et al. |
| 5,641,323 A | 6/1997 | Caldarise |
| 5,658,338 A | 8/1997 | Tullos et al. |
| 5,658,348 A | 8/1997 | Rohr, Jr. |
| 5,676,704 A | 10/1997 | Ries et al. |
| 5,702,474 A | 12/1997 | McCandliss |
| 5,702,475 A | 12/1997 | Zahedi |
| 5,702,477 A | 12/1997 | Capello et al. |
| 5,702,478 A | 12/1997 | Tornier |
| 5,709,688 A | 1/1998 | Salyer |
| 5,871,548 A | 2/1999 | Sanders et al. |
| 5,931,870 A | 8/1999 | Cuckler et al. |

FOREIGN PATENT DOCUMENTS

| | | |
|---|---|---|
| EP | 0 501 207 A1 | 9/1992 |
| EP | 0 563 503 A1 | 6/1993 |
| EP | 0 605 368 A1 | 7/1994 |
| EP | 0 846 453 A3 | 6/1998 |
| FR | 2 578 162 | 9/1986 |
| FR | 2 595 241 | 9/1987 |
| FR | 2 633 823 | 1/1990 |
| FR | 2 634 372 | 1/1990 |
| FR | 2 660 546 | 10/1991 |
| WO | WO 94/23670 | 10/1994 |
| WO | WO 96/13231 | 5/1996 |

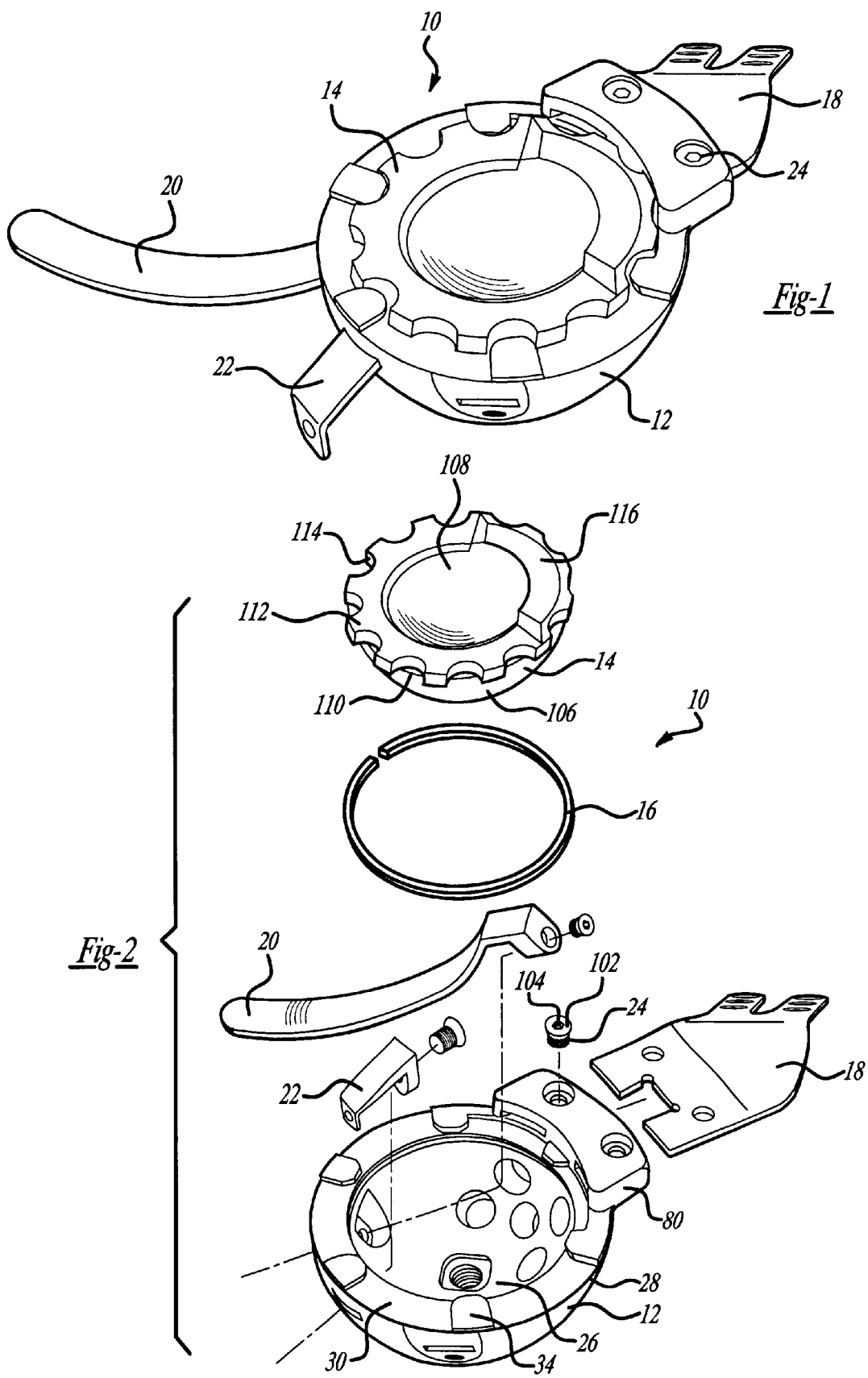

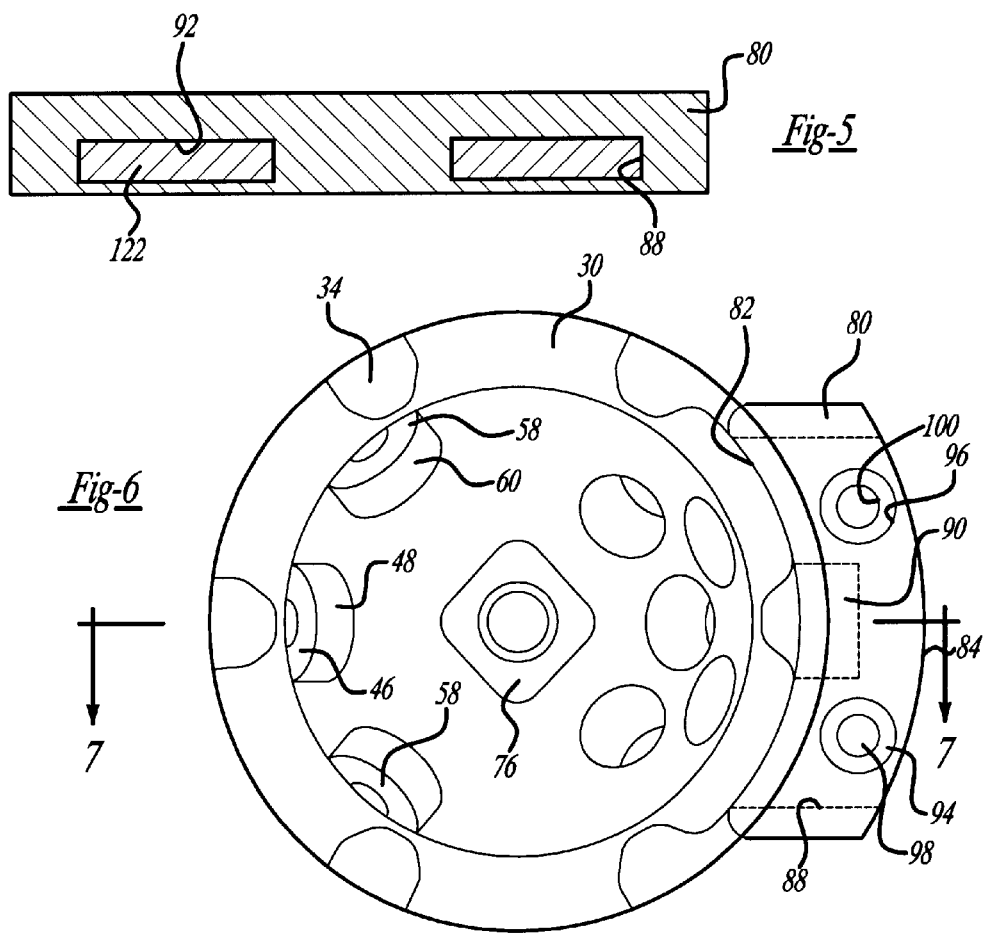
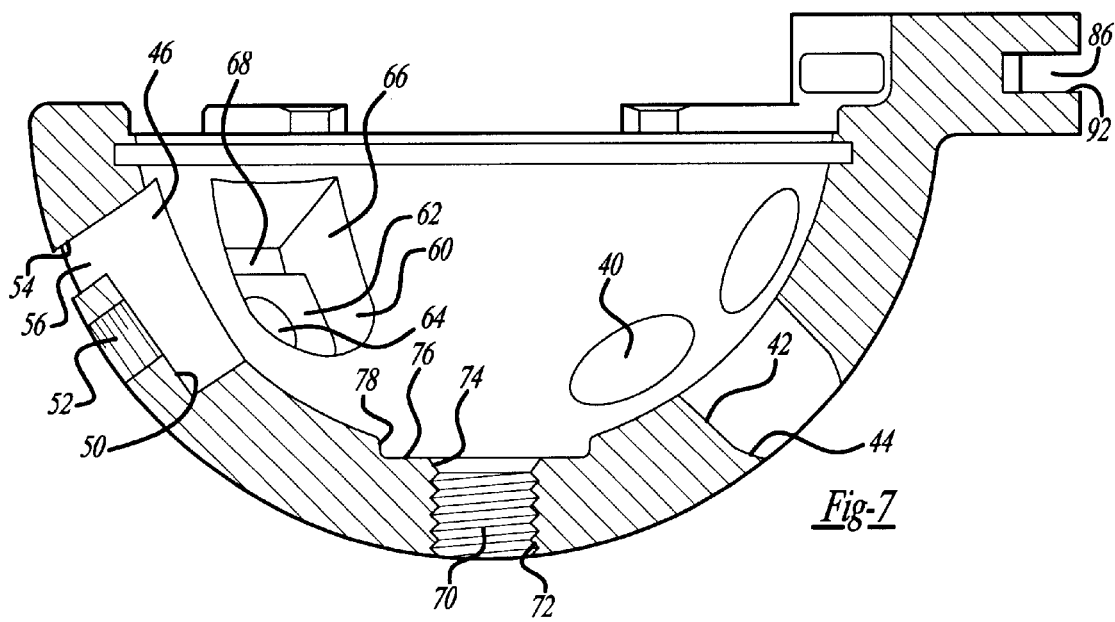

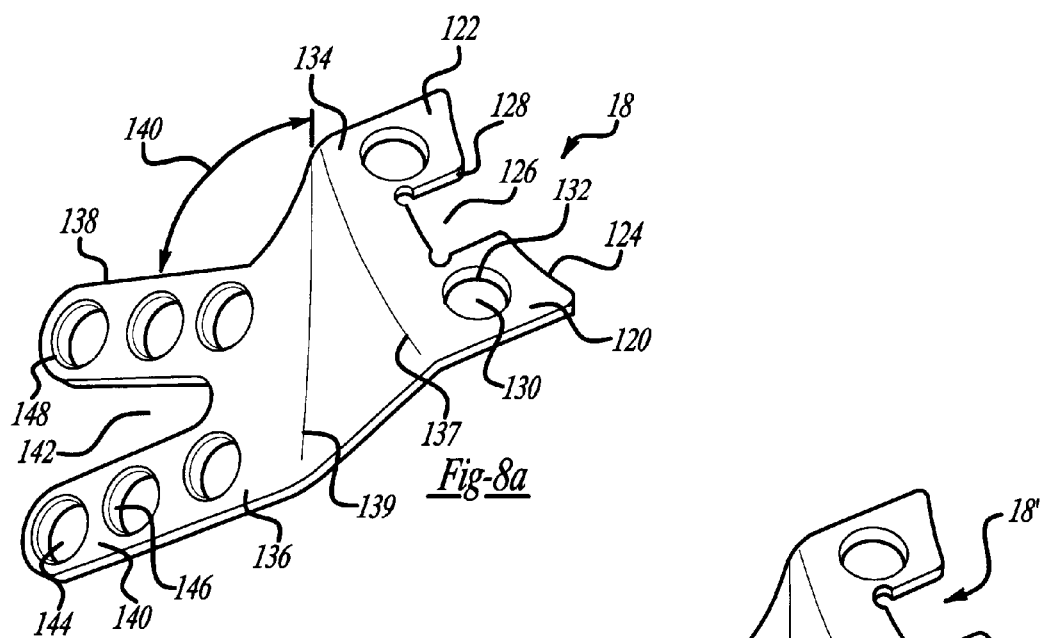
*Fig-8a*
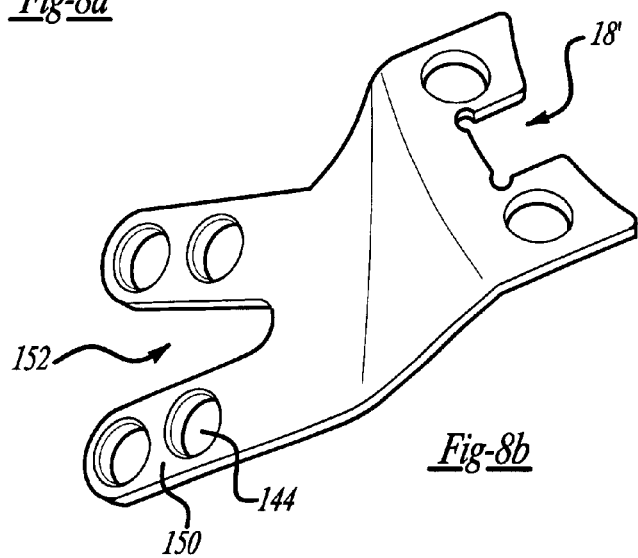
*Fig-8b*
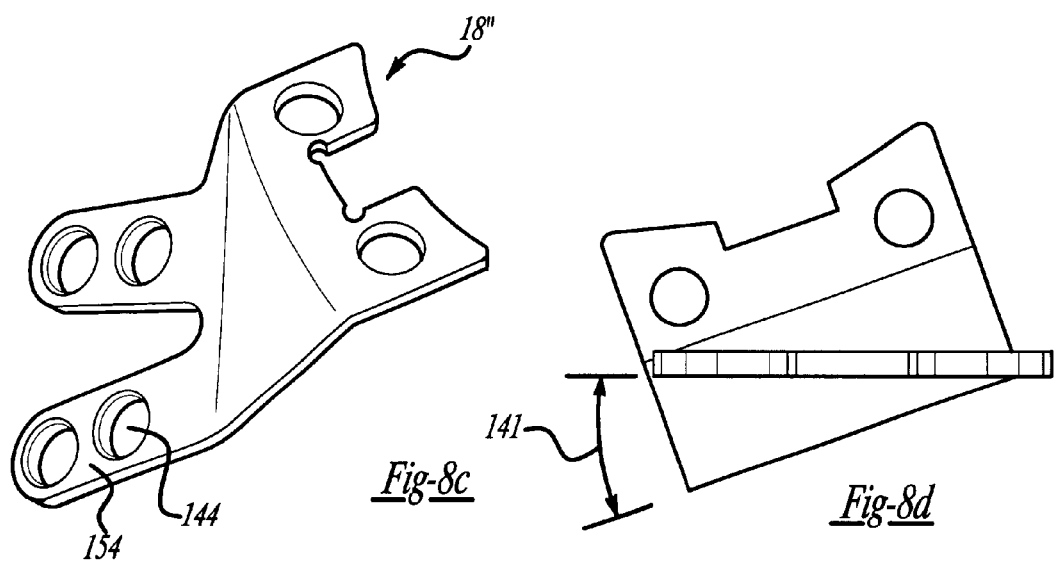
*Fig-8c*  *Fig-8d*

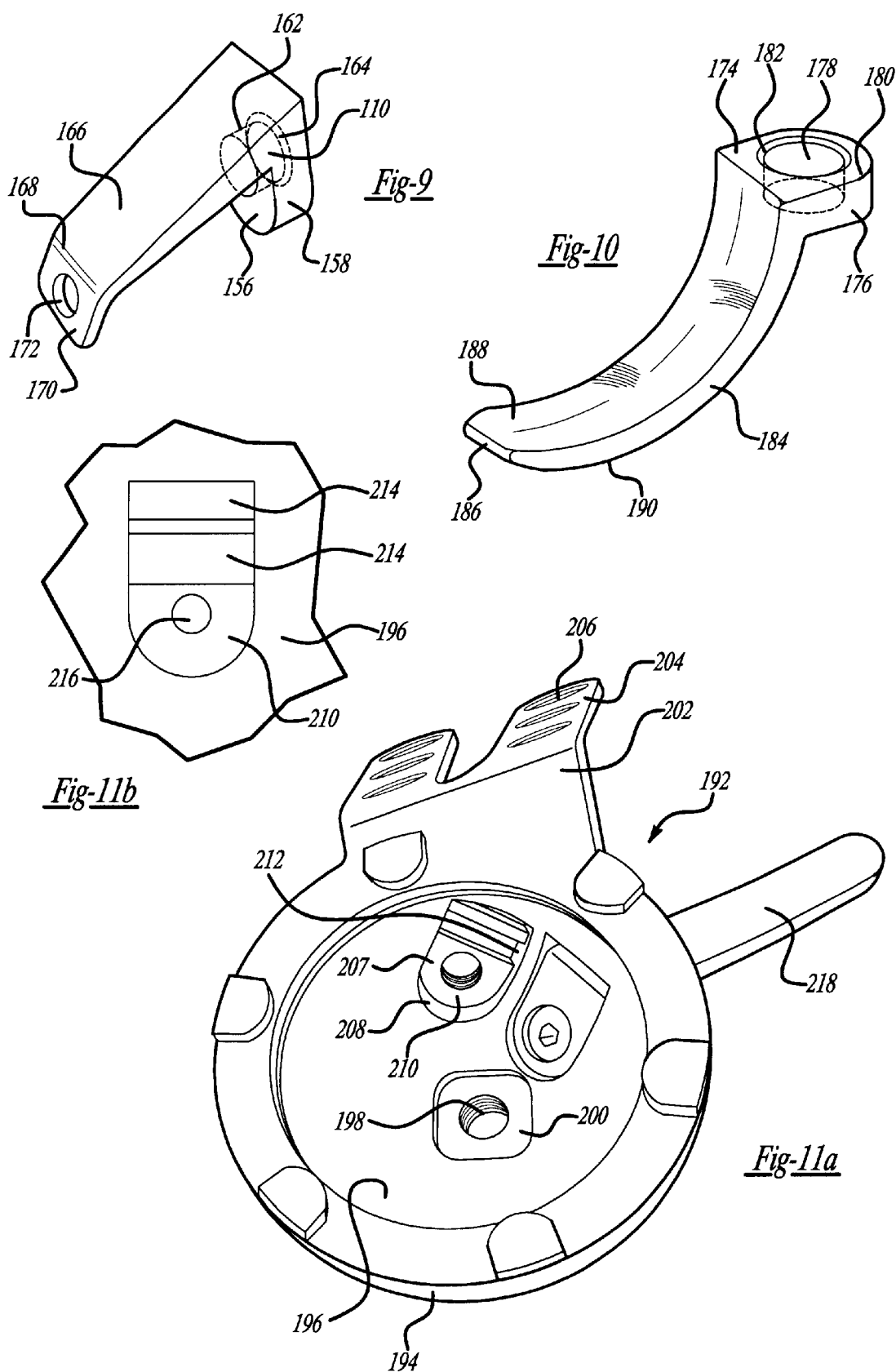

METHOD AND APPARATUS FOR PROVIDING A MODULAR ACETABULAR PROSTHESIS

This application claims the benefit of provisional application 60/127,023 filed Mar. 31, 1999.

BACKGROUND OF THE INVENTION

1. Field of the Invention

This invention relates generally to a method and apparatus for use in orthopedic surgery and, more particular, to a method and apparatus for providing a modular acetabular prosthesis having various modular attachment components for use during an orthopedic surgical procedure.

2. Discussion of the Related Art

A natural hip joint may undergo degenerative changes due to a variety of etiologies. When these degenerative changes become so far advanced and irreversible, it may ultimately become necessary to replace a natural hip joint with a prosthetic hip. When implantation of such a hip joint prosthesis becomes necessary, the head of the natural femur is first resected and a cavity is created within the intramedullary canal of the host femur for accepting the hip prosthesis. The hip prosthesis may be inserted and supported within the host femur by cementing the hip prosthesis within the host femur. Alternatively, the hip prosthesis may be impacted into the host femur so that it is snugly fit and supported by the host femur. If the acetabulum also needs repair, all remnants of articular cartilage are generally removed from the acetabulum and an acetabular prosthesis which will accommodate the head or ball of the hip prosthesis is affixed to the acetabulum. The acetabular prosthesis is affixed to the acetabulum by means of cement, screws or other appropriate fixation means.

Due to any number of reasons, however, a small portion of patients that undergo such orthopedic surgical procedures may require subsequent revision surgery to replace the prosthetic device with a new prosthetic device generally referred to as a revision prosthesis. In this regard, a revision acetabular prosthesis will generally include additional mounting points, such as integral flanges or hooks that provide additional stability for the revision acetabular prosthesis. These additional mounting points are generally required due to additional bone loss or defects exhibited at the acetabulum, such as collar/rim defects or pelvic discontinuity defects.

Various types of revision acetabular prostheses are currently available and different surgeons prefer different types of revision acetabular prostheses. Some surgeons prefer to use what is known as an ilium flange that is formed integral with the acetabular prosthesis and enables further securement of the acetabular prosthesis in the ilium region of the pelvis. Other surgeons prefer to use what is known as an obturator hook that is able to provide inferior fixation of the acetabular prosthesis by engaging the obturator foramen which is a large aperture adjacent the acetabulum. Because of this, a hospital must maintain a large inventory of different revision acetabular cups to meet the various surgeons' preferences. Moreover, the surgeon will generally have to have several revision acetabular cups available during surgery to account for any type of condition that may arise during the surgical procedure. This increased inventory of prosthetic devices increases the overall hospital costs and inventory control. Furthermore, by requiring the multiple revision acetabular cups to be available during the surgical procedure, multiple prosthetic devices must be sterilized prior to the surgical procedure, thereby increasing the surgical time, cost and complexity.

What is needed then is a method and apparatus for providing a modular acetabular prosthesis having various modular attachment components for use during an orthopedic surgical procedure. This will, in turn, provide more surgical flexibility during implantation of the acetabular prosthesis, provide the surgeon with a variety of surgical options at the time of the surgical procedure, provide a universal acetabular cup that can be configured for use in many circumstances, reduce hospital inventory and inventory tracking requirements, and reduce the overall surgical time, cost and complexity. It is, therefore, an object of the present invention to provide such a method and apparatus for providing a modular acetabular prosthesis having various modular attachment components for use during an orthopedic surgical procedure.

SUMMARY OF THE INVENTION

In accordance with the teachings of the present invention, the method and apparatus for providing a modular acetabular prosthesis having a modular attachment component for use in orthopedic surgery is disclosed. The acetabular prosthesis includes an acetabular cup and a variety of modular attachment components. In this regard, a surgeon can select the appropriate modular attachment components depending on the patients needs, thereby providing a versatile acetabular prosthesis.

In one preferred embodiment, an acetabular prosthesis for implantation in an acetabulum is provided. The acetabular prosthesis includes an acetabular cup, an anti-rotation counterbore and a modular attachment component. The acetabular cup has an outer surface which is operable to be received in the acetabulum and an inner surface which is operable to receive a bearing liner. The anti-rotation counterbore is defined by the inner surface of the acetabular cup. The modular attachment component has an attachment member and an engagement member. The attachment member is operable to substantially nest within the anti-rotation counterbore and the engagement member is operable to engage a region of the acetabulum, such that upon positioning the attachment member in the anti-rotation counterbore the modular attachment component is inhibited from rotational movement relative to the acetabular cup.

In another preferred embodiment, an acetabular prosthesis for implantation in an acetabulum includes an acetabular cup, an attachment plate and a modular attachment component. The acetabular cup has an outer surface which is operable to be received in the acetabulum and an inner surface which is operable to receive a bearing liner with an annular region extending between the outer and inner surfaces. The attachment plate extends from the annular region and defines an internal channel having an internal key position with the internal channel. The modular attachment component has an attachment member and an engagement member. The attachment member is operable to be slidably received within the channel and positioned about the internal key. The engagement member is operable to engage a region of the acetabulum, such that upon the attachment member being slidably received in the channel, the modular attachment component is inhibited from rotational movement relative to the acetabular cup.

In yet another preferred embodiment, an acetabular prosthesis for implantation in an acetabulum includes an acetabular cup, at least one slot defined by the acetabular cup and a modular attachment component. The acetabular cup has an outer surface which is operable to be received in the acetabulum and an inner surface which is operable to receive a bearing liner. The one slot passes through the acetabular cup from the inner surface to the outer surface. The modular attachment component has an attachment member and an elongated blade. The attachment member is operable for use in attaching the modular attachment component to the acetabular cup and the elongated plate is operable to pass through the one slot to provide intermedullary fixation of the acetabular cup in a region about the acetabulum.

In another preferred embodiment, an acetabular prosthesis for implantation in an acetabulum includes an acetabular cup, at least one bore defined by the acetabular cup, a rotational member and a modular attachment component. The acetabular cup has an outer surface which is operable to be received in the acetabulum and an inner surface which is operable to receive a bearing liner. The one bore passes from the inner surface to the outer surface and includes a rotational sidewall. The rotational member is operable to mate with at least a portion of the rotational sidewall of the bore. The modular attachment component is in communication with the rotational member, such that the modular attachment component is operable to be pivoted relative to the acetabular cup as the rotational member engages the rotational sidewall.

In yet another preferred embodiment, an acetabular prosthesis for implantation in an acetabulum includes an acetabular cup, a pivot bore, a plurality of engagement bores and a modular attachment component. The acetabular cup has an outer surface which is operable to be received in the acetabulum and an inner surface which is operable to receive a bearing liner. The pivot bore is defined by the acetabular cup and the plurality of engagement bores is also defined by the acetabular cup, such that the plurality of engagement bores is positioned circumferentially about the pivot bore and extending through the acetabular cup. The modular attachment component includes an attachment member and an engagement member. The attachment member is operable to be pivotably secured relative to the pivot bore and the engagement member is operable to engage a plurality of regions about the acetabulum.

In still another preferred embodiment, a method for implanting an acetabular prosthesis having a modular attachment component in the acetabulum is provided. This method includes providing an acetabular cup that has an outer surface and an inner surface, engaging the outer surface of the acetabular cup with a surgically prepared portion of the acetabulum, locating a punch guide along the inside surface of the acetabular cup, guiding a punch through the acetabular cup and into the acetabulum to form a hole in the acetabulum, removing the punch and punch guide from the acetabular cup, passing a portion of the modular attachment component through the acetabular cup and into the hole formed by the punch, and securing the modular attachment component to the acetabular cup.

Use of the present invention provides a method and apparatus for providing a modular acetabular prosthesis. As a result, the aforementioned disadvantages associated with the currently available acetabular prosthesis have been substantially reduced or eliminated.

BRIEF DESCRIPTION OF THE DRAWINGS

Still other advantages of the present invention will become apparent to those skilled in the art after reading the following specification and by reference to the drawings in which:

FIG. 1 is a perspective view of an assembled acetabular prosthesis according to the teachings of a first preferred embodiment of the present invention;

FIG. 2 is an exploded perspective view of the acetabular prosthesis of FIG. 1;

FIG. 5 is a cross-sectional view taken along line 5—5 of FIG. 3;

FIG. 6 is a top plane view of the acetabular cup;

FIG. 7 is a cross-sectional view taken along line 7—7 of FIG. 6;

FIG. 8a is a perspective view of a large right ilium flange;

FIG. 8b is a perspective view of a medium right ilium flange;

FIG. 8c is a perspective view of a small right ilium flange;

FIG. 8d is a front elevational view of the large right ilium flange;

FIG. 9 is a perspective view of an obturator hook;

FIG. 10 is a perspective view of an ischial blade;

FIG. 11a is a perspective view of an assembled acetabular cup and ilium blade according to the teachings of a second preferred embodiment of the present invention;

FIG. 11b is a planar view of a counterbore in the acetabular cup of FIG. 11a;

FIG. 12 is a perspective view of the ilium blade;

FIG. 13a is a cross-sectional view of an acetabular prosthesis having a swivel spike according to the teachings of a third preferred embodiment of the present invention;

FIG. 13b is a perspective view of a swivel member used in conjunction with the swivel spike of FIG. 13a;

FIG. 13c is a planar view of an instrument used to adjust and tighten the swivel spike of FIG. 13a;

FIG. 14b is a cross-sectional view taken along line 14b—14b of FIG. 14a;

DETAILED DESCRIPTION OF THE PREFERRED EMBODIMENT(S)

Figure 3:
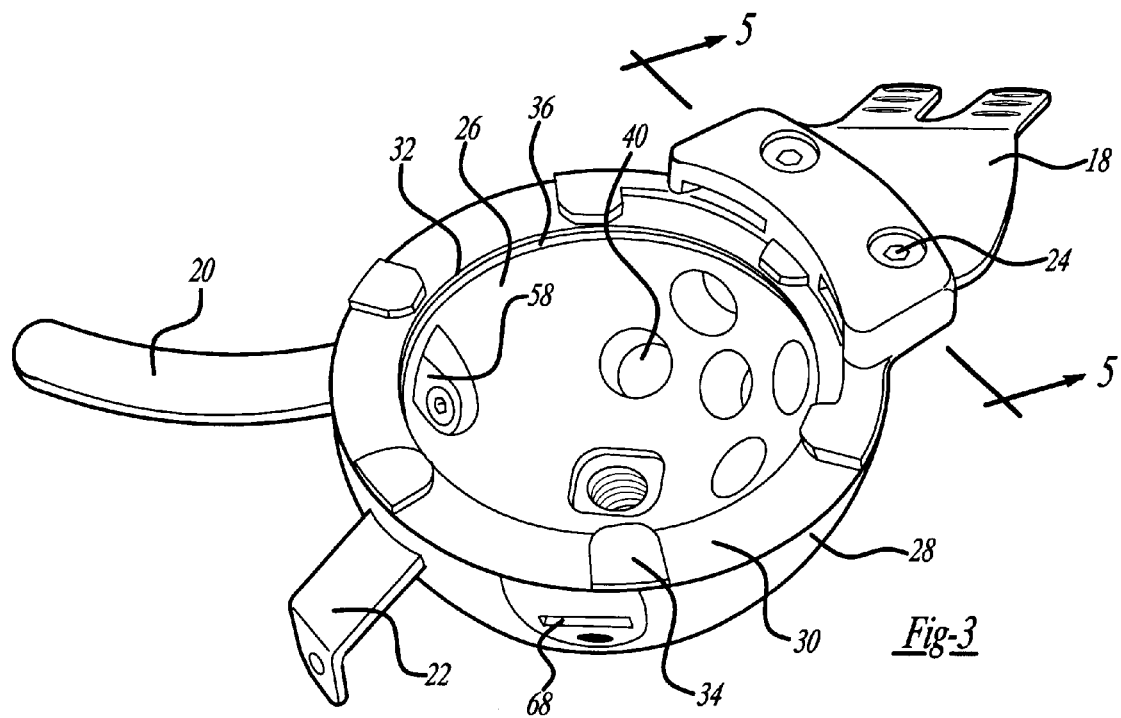
FIG. 3 is a first perspective view of an acetabular cup with modular attachment components of FIG. 1.

The following description of the preferred embodiments concerning a method and apparatus for providing a modular acetabular prosthesis for use in orthopedic surgical procedures are merely exemplary in nature and are not intended to limit the invention or its application or uses. Moreover, while the present invention is described in detail below with reference to performing a revision type implantation procedure, it will be appreciated by those skilled in the art that the present invention is clearly not limited to only revision type orthopedic surgical procedures and may be used with various other orthopedic surgical procedures as well.

Referring to FIGS. 1–2, an acetabular prosthesis 10 according to the teachings of a first preferred embodiment of the present invention is shown. The acetabular prosthesis 10 includes a full-hemisphere acetabular cup 12 having a congruent shell or bearing liner 14 retained within the cup 12, via a ring lock 16. The acetabular prosthesis 10 further includes a modular ilium flange 18, a modular ischial blade 20 and a modular obturator hook 22 each retained with threaded set screws 24.

Figure 4:
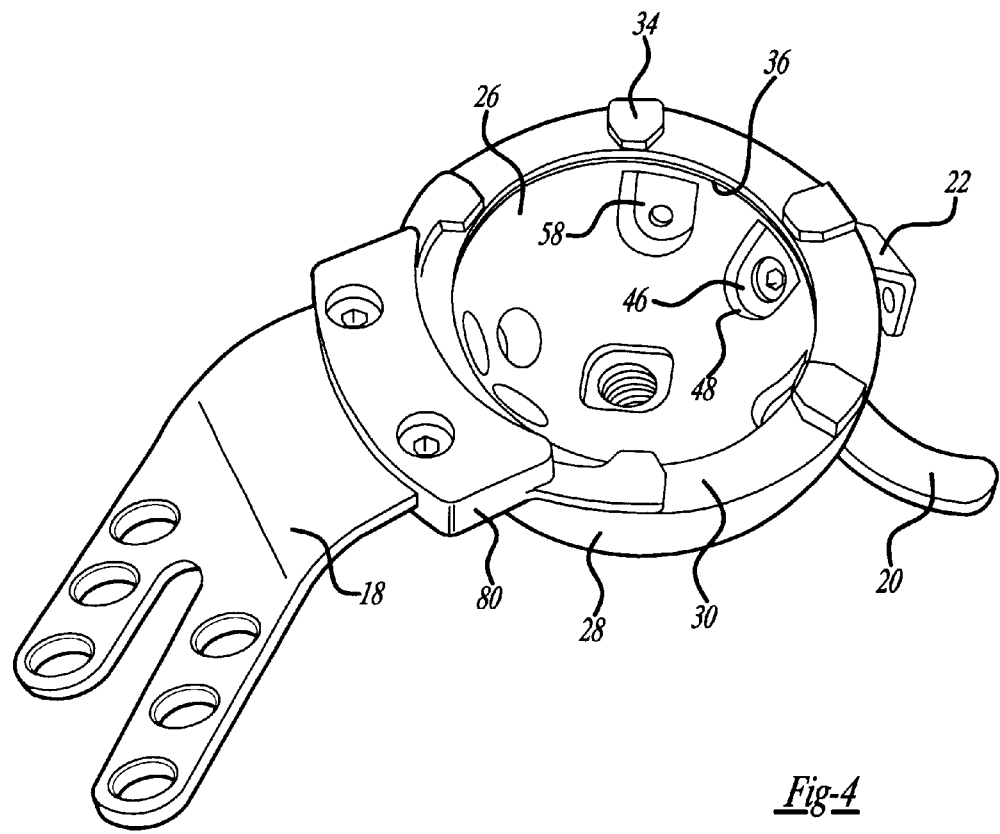
FIG. 4 is a second perspective view of the acetabular cup with modular attachment components of FIG. 1.

The acetabular cup 12, shown in further detail in FIGS. 3–4, includes a smooth inner concave surface 26 and a roughened or porous coated outer convex surface 28. The acetabular cup 12 is made from any suitable biocompatible material, such as titanium, stainless steel, titanium alloy, cobalt-chrome-molybdenum alloy, etc. and is preferably made of the titanium alloy Ti—6Al—4V. The acetabular cup 12 further includes an annular face 30 having a shoulder 32 and a plurality of arcuate alignment tabs 34. Located adjacent to the shoulder 32 is an annular groove 36 that is operable to snappingly receive the ring lock 16 to secure the bearing liner 14 within the concave surface 26 of the acetabular cup 12. The ring lock 16 is preferably the RingLoc® system offered by Biomet, Inc. of Warsaw, Ind. However, those skilled in the art will recognize that any other mechanism for securing the bearing liner 14 relative to the acetabular cup 12 may also be used such as cement, screws, etc.

Located within the inner surface 26 in the superior region of the acetabular cup 12 are a plurality of bone screw holes 40 that are defined by the acetabular cup 12. The bone screw holes 40 each include a first cylindrical sidewall 42 and a spherical tapered sidewall 44 (see FIG. 7). Each bone screw hole 40 is operable to receive a conventional bone screw to provide for fixed engagement with the acetabulum. The head of each bone screw used is flushly received within sidewalls 42 and 44.

Located directly inferiorly to the bone screw holes 40 is an anti-rotation obturator counterbore 46, also defined by the acetabular cup 12. The obturator counterbore 46 extends radially from the acetabular cup 12 and has a substantially D-shaped sidewall 48 and a stepped shoulder 50. Passing through the stepped shoulder 50 is a threaded bore 52 which is operable to threadably receive one of the threaded set screws 24. A rectangular shaped sidewall 54 extends from the concave surface 26 to the convex surface 28, to define a rectangular bore 56. The obturator counterbore 46 nestingly receives the obturator hook 22 to provide for rigid non-rotation fixation of the obturator hook 22 relative to the acetabular cup 12, further discussed herein. The obturator counterbore 46 thereby provides a surgeon with the option to utilize the obturator hook 22 for further securement relative to the obturator foramen should this be desired.

Positioned inferiorly and adjacent to the obturator counterbore 46 are a pair of anti-rotation ischial counterbores 58 also radially extending from the acetabular cup 12. Each ischial counterbore 58 includes a D-shaped sidewall 60, a stepped shoulder 62 having a threaded bore 64 and a rectangular sidewall 66 defining a rectangular bore 68. Each ischial counterbore 58 is operable to nestingly receive different size ischial blades 20 which are secured, via a threaded set screw 24, further discussed herein. Each counterbore 58 is located radially adjacent to the obturator counterbore 46 to provide for fixation of a right or left ischial blade 20. Therefore, the acetabular cup 12 may be used for both a right or left acetabulum by simply selecting the appropriate ischial counterbore 58.

It should further be noted that while the obturator counterbore 46 and the ischial counterbore 58 are shown having D-shaped sidewalls 48 and 60, it will be understood that any other shaped counterbore may also be provided that provides an anti-rotation effect. In other words, the D-shaped sidewalls 48 and 60 are elongated and include at least one corner which prevents rotation of the particular modular attachment component within these counterbores. However, square, rectangular, elongated elliptical, triangular or any other shapes which provides at least one corner or are elongated along one plane will provide the anti-rotation effect desired in contrast to merely circular bores which generally cannot inhibit this anti-rotation effect.

Passing centrally through the acetabular cup 12 is a threaded bore 70 defined by a cylindrical threaded sidewall 72 and a conical taper 74. A substantially square counterbore 76 defined by sidewall 78 is concentric with the bore 70 and located on the inside concave surface 26. The threaded bore 70 is operable to threadably receive an insertion tool which is nestingly received within the square counterbore 76 for use during insertion of the acetabular cup 12, further discussed herein. While each of the bores passing from the inner concave surface 26 to the outer concave surface 28 are shown open, mating plugs may also be pre-assembled with the acetabular cup 12 to seal the bores. In this way, debris may be inhibited from migrating between the acetabular cup 12 and the liner 14.

Extending from the annular surface 30 is an attachment plate 80. The attachment plate 80 is located superiorly and adjacent to the bone screw holes 40. The attachment plate 80 includes a concave surface 82 operable to nestingly mate with the bearing liner 14 and a convex surface 84 operable to slidably receive the ilium flange 18. Passing through the sidewalls 84 and 82 is a channel 86 defined by inner parallel sidewalls 88 and an internal rectangular key 90. The channel 86 further includes a pair of parallel top and bottom sidewalls 92. Passing transversely through the attachment plate 80 are a first pair of counterbores 94 defined by sidewalls 96 and a second pair of threaded bores 98 defined by threaded sidewalls 100. The channel 86 is operable to slidably receive different size ilium flanges 18 for either the right or left ilium. The channel 86 slidably captures the ilium flange 18 and the internal key 90 inhibits rotation of the flange 18 relative to the acetabular cup 12. Once inserted, a pair of threaded set screws 24 are threadably received within threaded bores 100 with the head 102 of the set screws 24 nestingly received within counterbores 94. The set screws 24 may be threadably received within the various threaded bores, via a hex head drive 104 or any other appropriate drive head.

The shell liner 14 is preferably formed from polyethylene or other suitable liner material. The shell liner 14 includes an outer convex surface 106 and an inner concave surface 108. The outer convex surface 106 is fully congruent and mates with the inner concave surface 26 of the acetabular cup 12 to minimize relative motion between the components. The inner concave surface 108 creates a uniform thickness of the shell liner 14 and acts as a bearing surface for a head of a hip prosthesis so as to dissipate stresses over the entire shell liner 14. The shell liner 14 is secured to the acetabular cup 12 by means of the ring lock 16 that engages a groove 110 formed into the shell liner 14, as well as the groove 36 formed into the acetabular cup 12. The ring lock 16 substantially reduces or eliminates micro-motion between the acetabular cup 12 and the shell liner 14 and is again preferably the RingLoc® system offered by Biomet, Inc. of Warsaw, Ind. The shell liner 14 also includes an annular lip 112 having arcuate notches 114 that nestingly mate with arcuate alignment tabs 34. The annular lip 112 further includes a stepped region 116 to provide further support for the head of a hip prosthesis, which is aligned generally in the superior region of the acetabular cup 12.

Turning to FIGS. 8a–8c, perspective views of a large right ilium flange 18, a medium right ilium flange 18' and a small right ilium flange 18" are shown. In this regard, like references numerals will be used to identify like structures with respect to each of the ilium flanges 18, 18' and 18". Each of the ilium flanges 18, 18' and 18" are preferably formed from commercially pure and malleable titanium or any other biocompatible material which is operable to be further formed and shaped to the contour of the patient. While right ilium flange 18, 18' and 18" are shown herein, left ilium flanges will also be provided.

The ilium flange 18 includes an attachment member 120 having a pair of slotted wings 122 that are slidably and nestably received within the channel 86 (see FIG. 5). Each wing 122 includes an arcuate sidewall 124 that mates substantially flush with the arcuate sidewall 82 in the attachment member 80. A notch region 126 defined by sidewall 128 nestingly mates about the internal key 90. Passing through each wing 122 is a bore 130 defined by cylindrical sidewall 132. Upon the notch region 126 nestingly engaging the key 90, the bores 130 are positioned substantially concentric with the bores 94 and 96. In this regard, once the ilium flange 18 is slidably received within the channel 86, via the attachment member 120, a pair of set screws 24 are threadably received within the threaded bores 100 and extend through the bores 130 with the head 102 of the set screws 24 nesting within the counterbores 94. This two point contact, along with the central internal key 90 provides a substantially rigid connection between the modular ilium flange 18 and the acetabular cup 12, thereby substantially inhibiting any rotational or micro-motion between the flange 18 and the acetabular cup 12.

The ilium flange 18 further includes a first substantially planar region 134 associated with the attachment member 120 and a second substantially planar engagement region 136 located at the distal end of the flange 18. A first bend region 137 angles at about 45° from the first planar region 134. A second bend region 139 extends 90° relative to sidewall 138 and is identified by reference numeral 140. The ilium flange 18 is twisted about 20° at the bend region 139, identified by reference numeral 141, and shown in FIG. 8d.

The planar region 136 includes a pair of angled fingers 140 having a central notch 142. Each finger 140 includes three bores 144 defined by cylindrical sidewalls 146 and tapered counterbores 148. Each bore 144 is operable to nestingly and flushly receive a bone screw to provide additional support for the acetabular cup 12 in the ilium region of the acetabulum.

Referring to FIGS. 8b and 8c, the medium right ilium flange 18' and the small right ilium flange 18" are shown. The ilium flanges 18' and 18" are substantially the same as the ilium flange 18, except that the ilium flange 18' includes a pair of fingers 150 that are shorter in length than the fingers 140 and has a deeper notch 152. Each finger 150 also includes only two bores 144. The ilium flange 18" also includes two fingers 154 which are shorter than the fingers 150 and include a pair of bores 144. It should further be noted that while right ilium flanges 18–18" are shown herein, the left ilium flanges will also be provided and shaped substantially similar to the right ilium flanges, except that the fingers 140 will angle opposite as shown in FIGS. 8a–8c. Moreover, while each ilium flange 18, 18' and 18" is shown having a pair of angled fingers, various other shapes for the flange may also be provided.

Turning to FIG. 9, the obturator hook 22 is shown in further detail. The obturator hook 22 includes an attachment member 156 having a D-shaped sidewall 158 which mates with the obturator counterbore 46. The attachment member 156 further defines a bore 160 passing therethrough having a cylindrical sidewall 162 and a tapered sidewall 164. The bore 160 aligns substantially concentric with the bore 52 when the D-shaped sidewall 158 is nestingly received within the obturator counterbore 46. Extending substantially perpendicular to the attachment member 156 is a first engagement member 166 that bends at region 168 to a second engagement member 170. Passing through the engagement member 170 is a bore 172. The obturator hook 22 is preferably formed from commercially pure titanium or any other biocompatible material that is preferably malleable. In this regard, the bore 172 enables a prying or adjustment instrument to be inserted into the bore 172 such that the surgeon can further deform the obturator hook 22 about the obturator foramen. Here again, a threaded set screw 24 is used to rigidly fix the obturator hook 22 to the acetabular cup 12, via the mating and congruent D-shaped sidewall 158 and D-shaped sidewall 48. This D-shaped anti-rotation mating surface further inhibits any rotational movement of the obturator hook 22 relative to the acetabular cup 12.

Referring to FIG. 10, the ischial blade 20 is shown in further detail. The ischial blade 20 is also preferably formed from a Ti—6Al—4V titanium alloy or any other appropriate biocompatible material. The ischial blade 20 includes an attachment member 174 having a D-shaped sidewall 176 that nestingly mates with either of the ischial counterbores 38. Extending through the attachment member 174 is a bore 178 having a cylindrical sidewall 180 and a tapered sidewall 182. The ischial blade 20 further includes an elongated arcuate engagement blade member 184 having a radius of preferably about 1.5 inches which conforms with the contour of the ischium. The elongated blade member 184 includes a distal tip 186 and parallel arcuate faces or sidewalls 188 and 190 to provide for additional structural integrity of the blade member 184.

Here again, the elongated blade member 184 is slidably received within rectangular bore 68, while the attachment member 174 is nestingly received within the ischial counterbore 58 (see FIG. 3). A set screw 24 is then threadably received within threaded bore 64 to snugly and rigidly secure the ischial blade 20 relative to the acetabular cup 12. By providing both a right and a left ischial counterbore 58, a surgeon can use the same acetabular cup 12 and insert the ischial blade 20 for use in a right or left ischium region of an acetabulum. Moreover, the D-shaped sidewall 176 nesting within the D-shaped sidewall 60 also inhibits rotational movement of the ischial blade 20 relative to the acetabular cup 12. It should be noted that both the ischial blade 20 and the obturator hook 22 may be polished, porous coated or have any other appropriate surface. The ischial blade 20 may also be provided in multiple lengths having approximately the same radius to accommodate different size patients.

An acetabular cup 192 according to the teachings of a second preferred embodiment of the present invention is shown in FIG. 11. The acetabular cup 192 also includes an outer convex porous coated surface 194 and an inner concave polished surface 196. Passing axially through the center of the acetabular cup 192 is a threaded bore 198 having the square counterbore 200 which is operable to receive the insertion tool. Extending superiorly from the acetabular cup 192 is an integral ilium flange 202 having a pair of fingers 204. Passing through the ilium flange 202 are a plurality of bores 206 operable to receive bone screws to retain the ilium flange 202 adjacent the ilium region of the acetabulum. Also positioned superiorly in the acetabular cup 192 are a pair of anti-rotation ilium counterbores 207 which are operable to receive an ilium blade 218. Here again, each ilium counterbore 207 includes a D-shaped sidewall 208, a stepped portion 210, a rectangular sidewall 212 and a rectangular bore 214. Passing through the stepped portion is a threaded bore 216.

It should also be noted that the ilium counterbore 207 includes two bores 214 that are aligned substantially parallel to one another and passing through the acetabular cup 192. Additionally, each ilium counterbore 207 is aligned substantially parallel to one another and does not extend radially from the center of the acetabular cup 192, but are aligned in the ilium region of the acetabulum. This provides the surgeon with an opportunity to insert an ilium blade 218 in different regions of the ilium and also either shallower or deeper relative to the ilium, depending upon which rectangular bore 214 is used. In this regard, the ilium counterbores 207 or any other counterbores may be aligned in the ilium region, the ischium region or the pubis region of the acetabulum and the acetabular cup may include multiple parallel bores for each of these regions to provide even further versatility of the particular acetabular cup.

Figures 12, 13A, 13B:
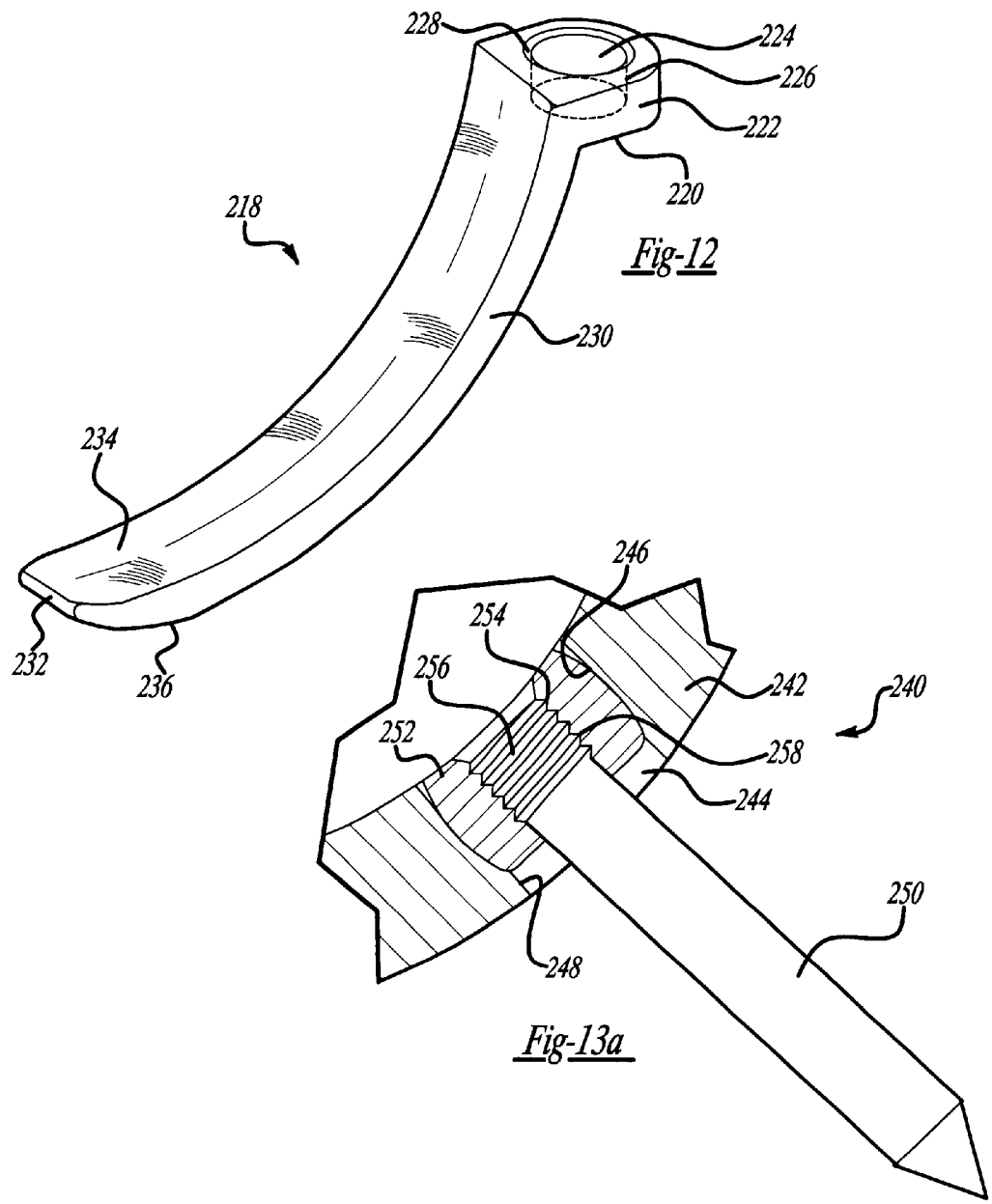
Figure 13C:
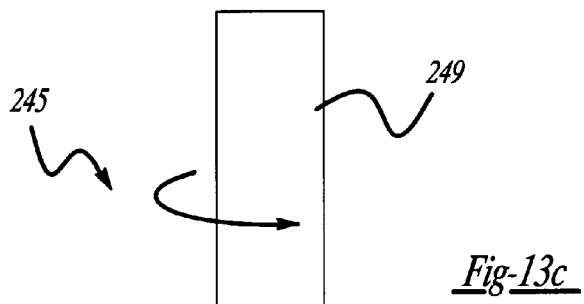
Figure 13D:
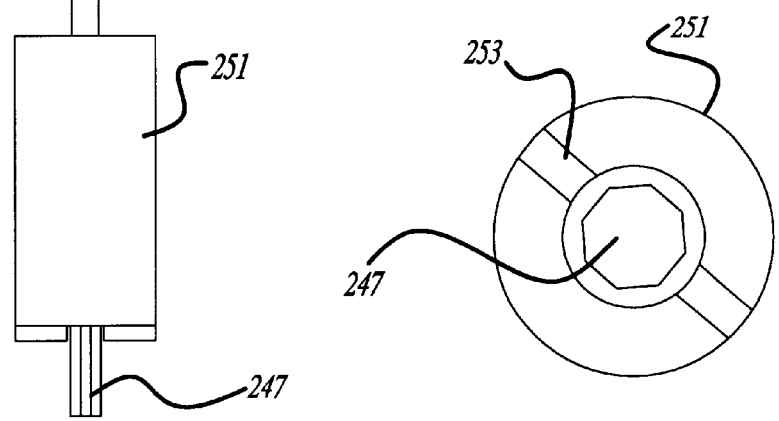
FIG. 13d is a bottom planar view of the instrument of FIG. 13c.

Turning to FIG. 12, a perspective view of the ilium blade 218 is shown. The ilium blade 218 includes an attachment member 220 having a D-shaped sidewall 222 and a bore 224. The bore 224 is defined by a cylindrical sidewall 226 and a spherical sidewall 228. The attachment member 220 will come in one of two lengths to permit an engagement blade member 230 to extend through one of the two bores 214. The blade member 230 is arcuately shaped about a radius of about six (6") inches and includes a distal tip 232 and parallel arcuate sidewalls 234 and 236. The shallower radius for the blade member 230 corresponds to the contour of the ilium. Here again, different length blades, as well as different depth blades relative to the opening 214 may be provided to accommodate for different size patients. Moreover, the ischial counterbores 58 may also include additional bores to allow for depth adjustment of the ischial blade 20.

While the acetabular cup 12 has been shown to have a modular ilium flange 18, a modular ischial blade 20 and a modular obturator hook 22 and the acetabular cup 192 has been shown to have an integral ilium flange 202 and a modular ilium blade 218, it is contemplated that any combination of these features may be incorporated into different acetabular cups. In this regard, an acetabular cup may include both modular ilium blades and ischium blades, as well as a modular obturator hook with either an integral or modular flange. Alternatively, an acetabular cup may have a modular ilium flange and a modular obturator hook only. Moreover, the bone screw holes 40 may also be positioned in various regions or eliminated altogether. This provides the versatility of having single universal acetabular cups which can be configured in many different ways to support many different needs and requirements.

Referring to FIGS. 13a–13d, an acetabular prosthesis 240 according to the teachings of a third preferred embodiment of the present invention is shown. The acetabular prosthesis 240 includes an acetabular cup 242 defining a bore 244 having a spherical sidewall 246 and a cylindrical sidewall 248. A spike 250 extends from the acetabular cup 242 and is rigidly retained within the acetabular cup 242 by way of a rotatable or pivotable ball 252 and a threaded interference 254. Alternatively, a blade may be substituted for the spike 250. The threaded interference 254 includes threaded sidewall 256 formed from the spike 250 and a threaded sidewall 258 formed from the rotatable ball 252. The rotatable ball 252 further includes four (4) expansion slots 241 and a pair of engagement notches 243. The expansion slots 241 enables the rotatable ball 252 to expand to fixedly engage the sidewall 248. The notches 243 enables an instrument 245 to engage and prevent the rotatable ball 252 from rotating upon tightening the spike 250.

To adjust the angle of the spike 250 relative to the acetabular cup 242, the spike 250 is simply rotated or moved within bore 244, as the rotatable ball 252 rotates therein. Once the appropriate angular position is located, a surgeon will simply thread the spike 250 into the rotatable ball 252, via a hex head drive 256 or any other appropriate drive member. As the spike 250 threadably engages the threaded bore 258 of the rotatable ball 252, the rotatable ball 252 expands, via the expandable slots 241, to fixedly secure the spike 250 relative to the cup 242. The spike 250 may also be threaded into the ball 252 so that it is still capable of rotation relative to the cup 242 but prevented from passing into the inside of the cup 242. The bore 244 can be positioned in the acetabular cup 242 at any desired location or a plurality of bores 244 may be provided. Here again, the swivel spike 250 may be incorporated into any of the embodiments of the acetabular cups shown herein and include any combination of modular attachment components.

The instrument 245 includes a hex head drive socket 247 extending from a handle 249. A cylindrical tube 251 passes over the hex head drive 247 and includes a pair of opposed keys 253 which are sized to engage the notches 243. In this regard, a surgeon will hold the sleeve 251 while engaging the keys 253 into notches 243. Once the rotatable ball 252 is retained in this manner, a surgeon will simply rotate the handle 249, thereby rotating the hex drive 247 to tighten the spike 250 within the rotatable ball 252. As this occurs, the rotatable ball expands via the expansion slots 241 to rigidly and fixedly secure the spike 250 relative to the acetabular cup 242.

Figure 14A:
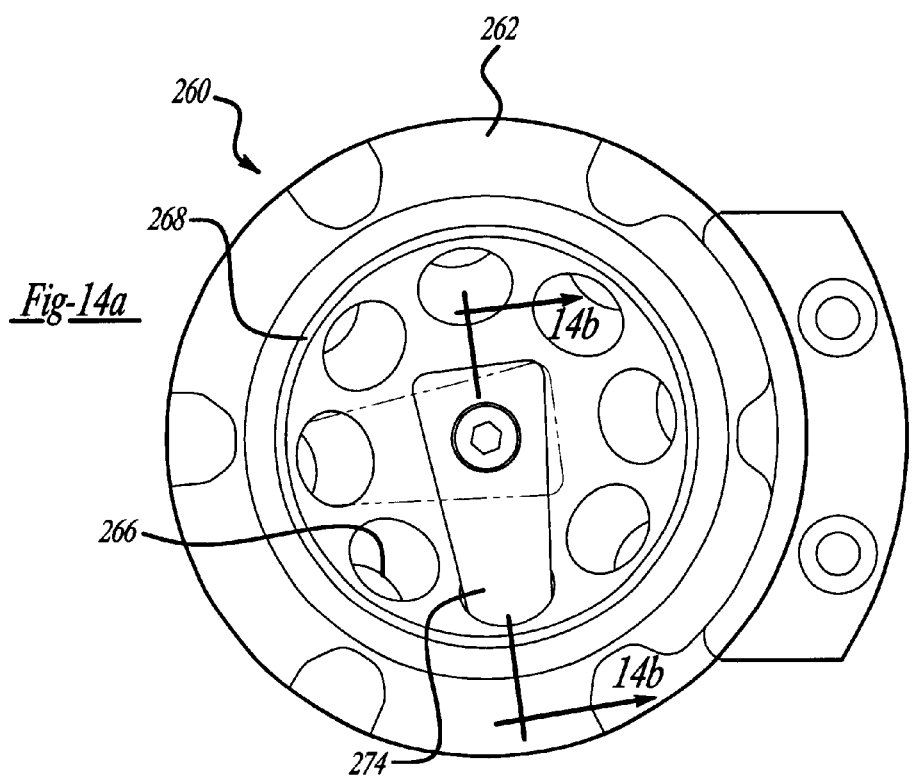
FIG. 14a is a top elevational view of an acetabular prosthesis having an index spike according to the teachings of a fourth preferred embodiment of the present invention.
Figure 14B:
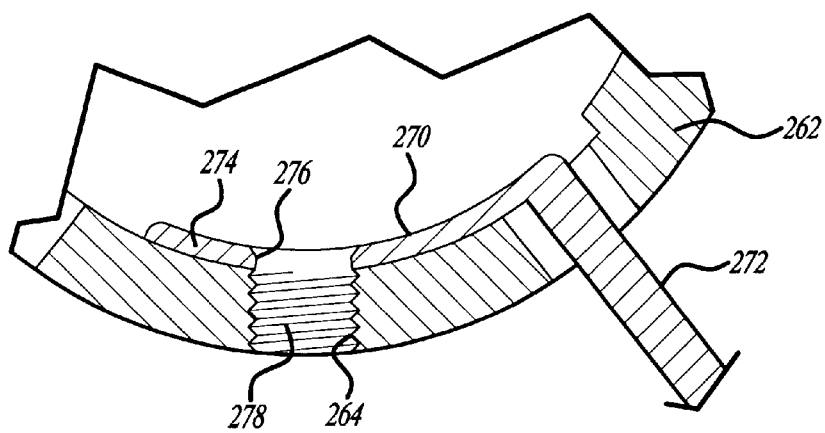

An acetabular prosthesis 260 according to the teachings of a fourth preferred embodiment of the present invention is shown in FIG. 14a and 14b. The acetabular prosthesis 260 includes an acetabular cup 262 having a threaded pivot centerbore 264. Located about the pivot centerbore 264 is a plurality of through bores 266, each positioned radially about centerbore 264 and within a concentric circular counterbore 268. A rotational modular attachment component 270 having an elongated spike member 272 and an attachment member 274 is operable to nestingly and rotatably be received within the counterbore 268. The attachment member 274 angles relative to the sphere member 272 at an angle of about 135° and includes a bore 276. The bore 276 is operable to nestingly receive a bolt 278 that is threadably received within the threaded bore 264. In use, a surgeon simply aligns the spear member 272 with the appropriate and desired hole 266 and nestingly seats the attachment member 274 within the counterbore 268. Once nestingly received and pivotably adjusted within the counterbore 268, the threaded bolt 278 is extended through the bore 276 and threadably received within the threaded bore 264. This enables the spike member 272 to be located at a plurality of regions about the acetabulum.

Figure 15:
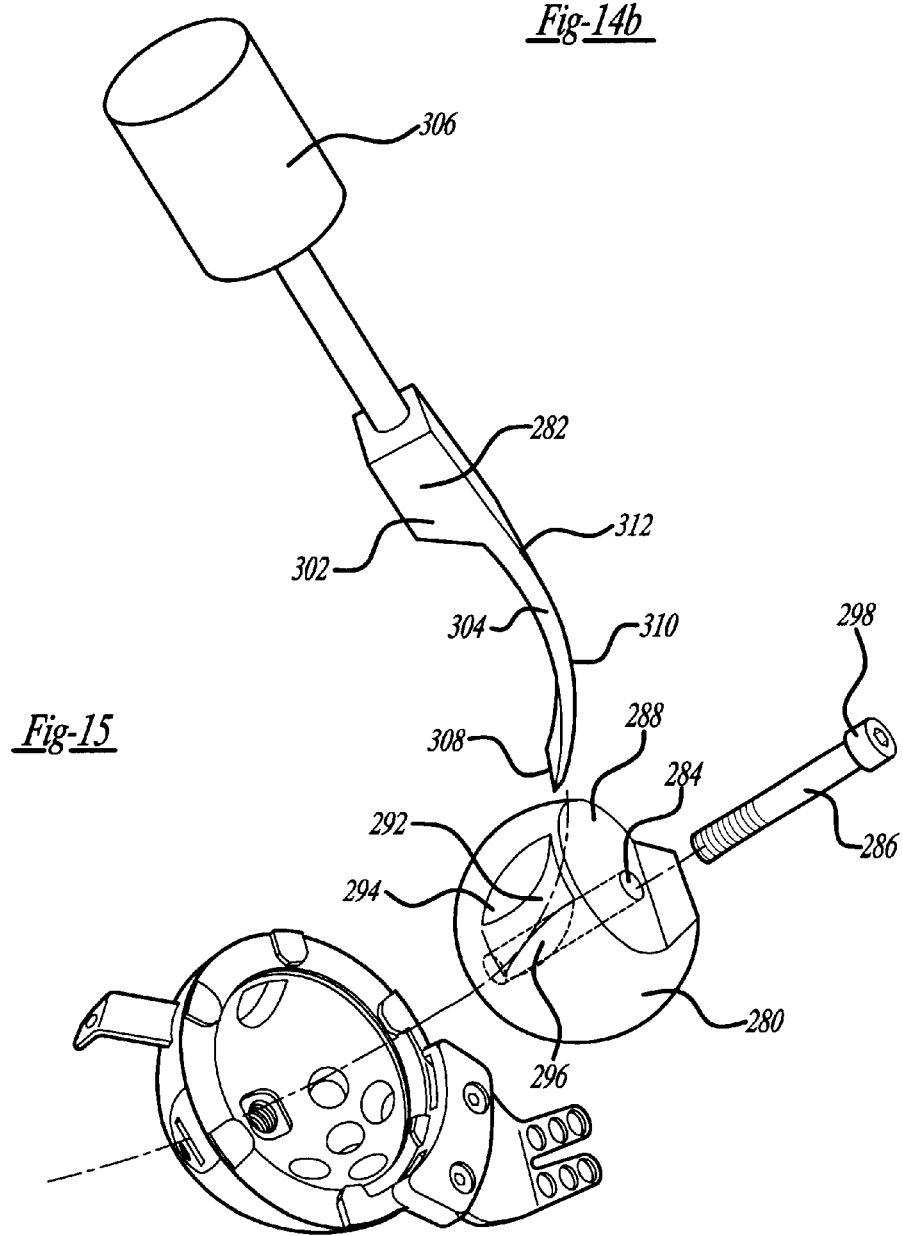
FIG. 15 is an exploded perspective view of a blade guide and punch used for implanting a modular attachment component.
Figure 16:
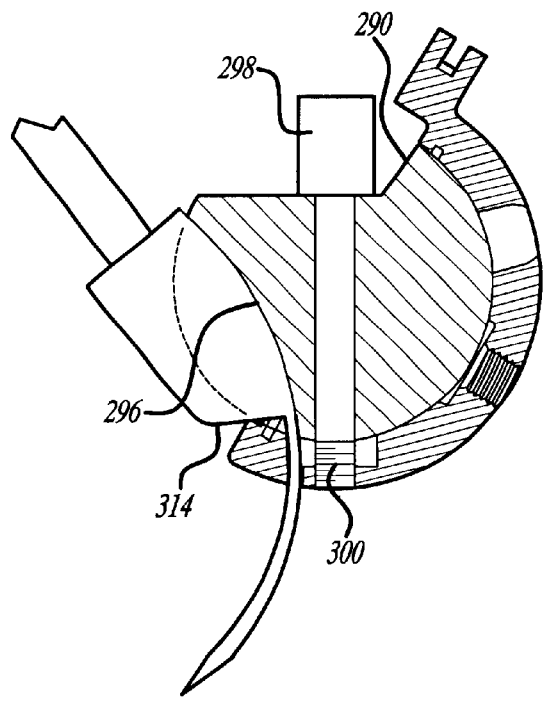
FIG. 16 is a cross-sectional assembled view of the blade guide and punch of FIG. 15.
Figure 17A:
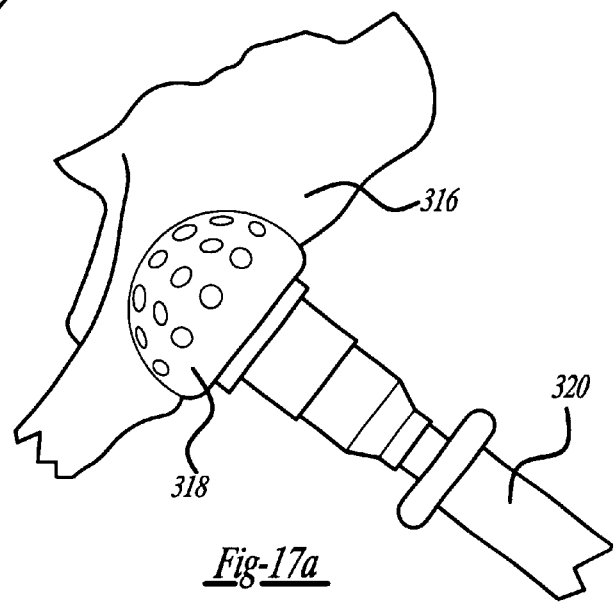
FIGS. 17a–17h illustrate a method for implanting the acetabular prosthesis according to the teachings of the first preferred embodiment of the present invention.
Figure 17B:
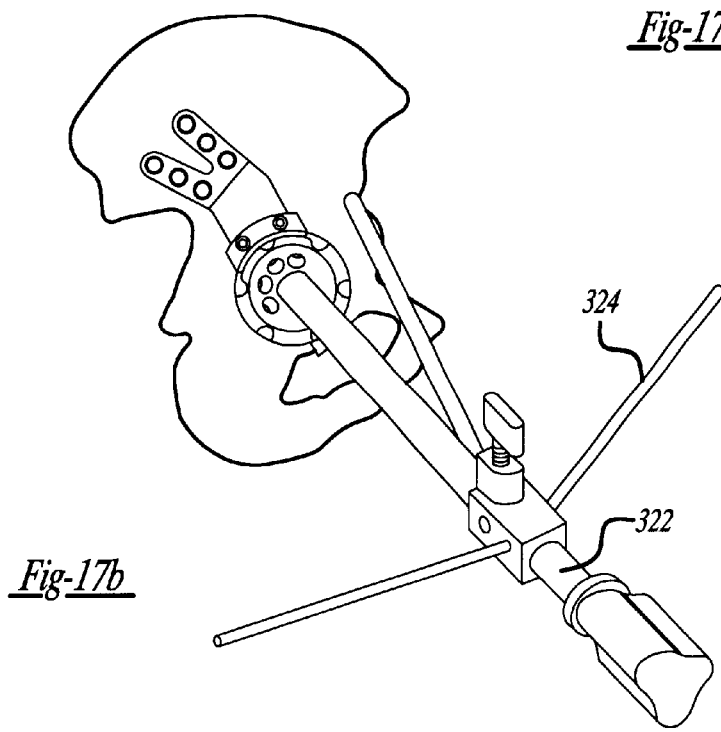
Figure 17C:
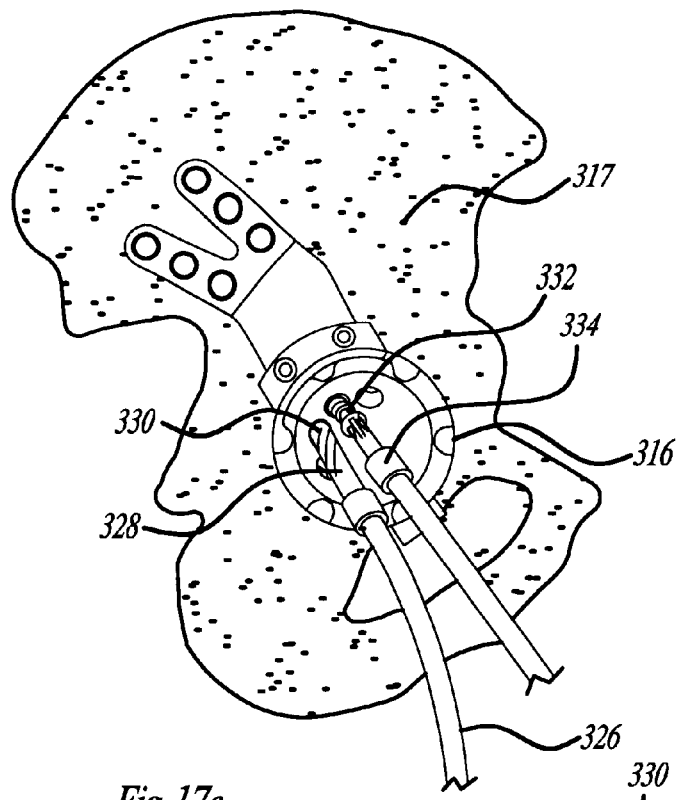
Figure 17D:
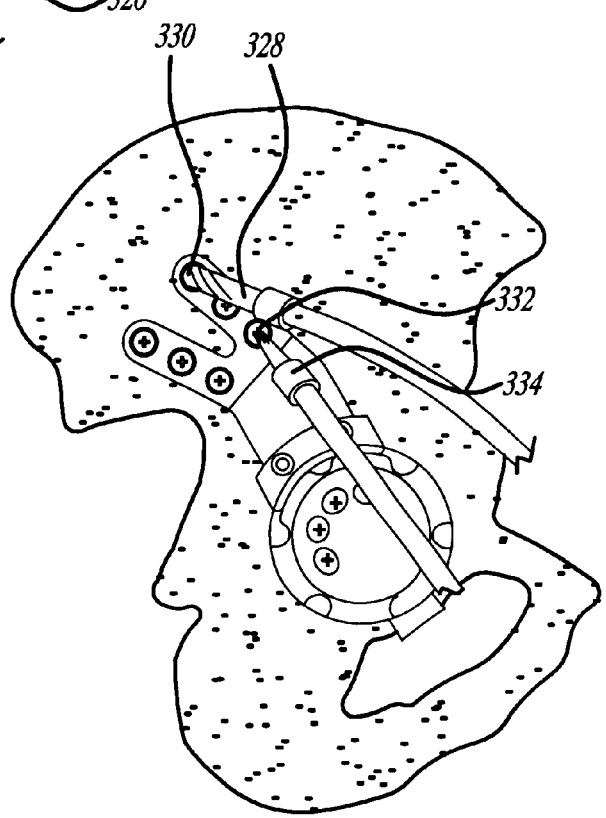
Figure 17E:
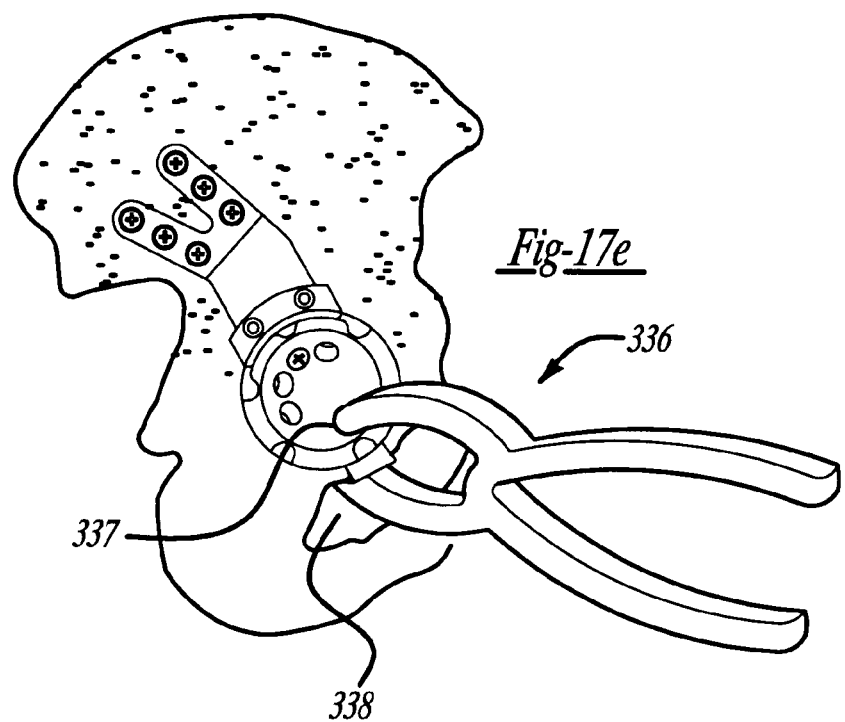
Figure 17F:
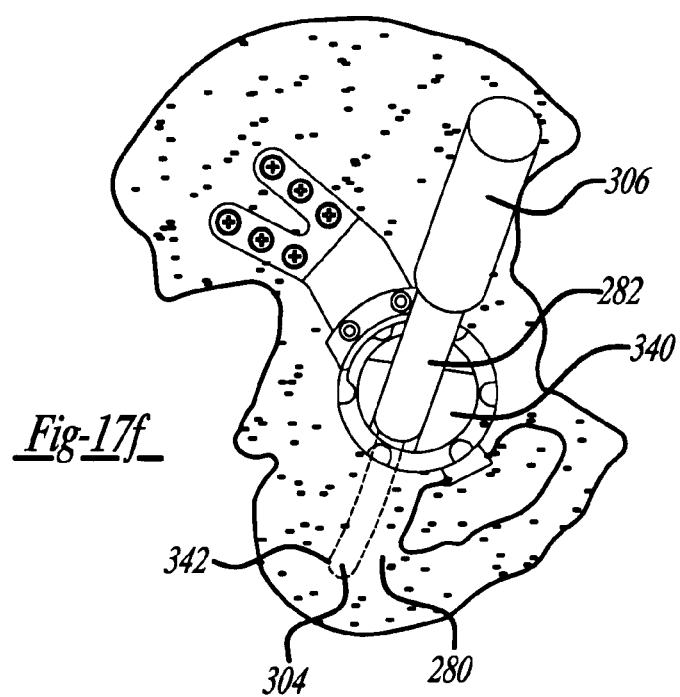
Figure 17G:
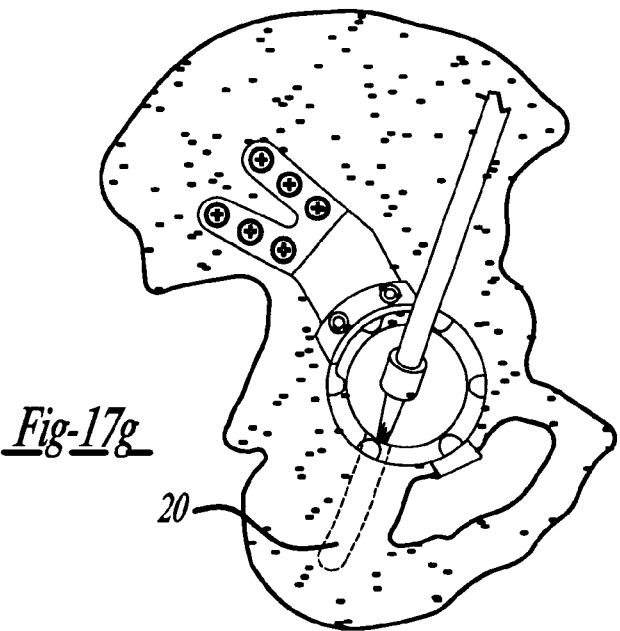
Figure 17H:
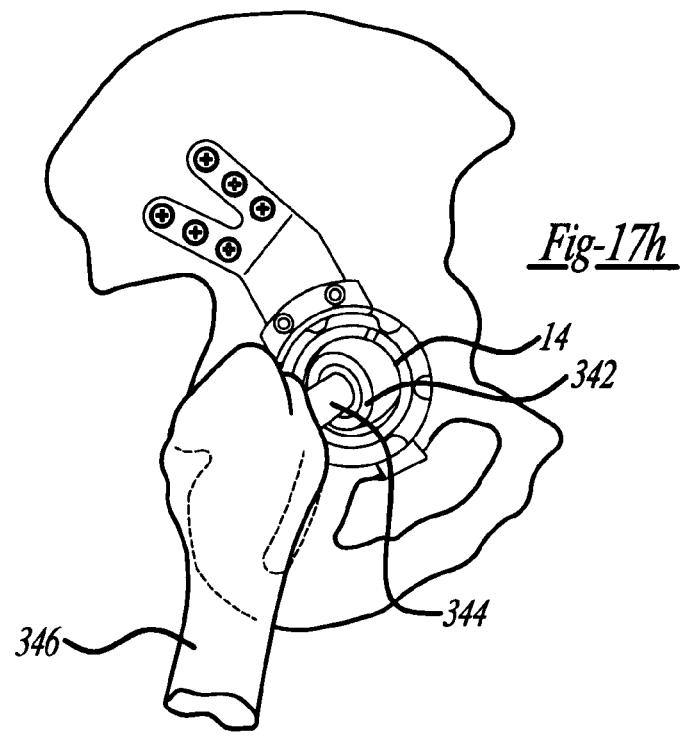
Figure 18:
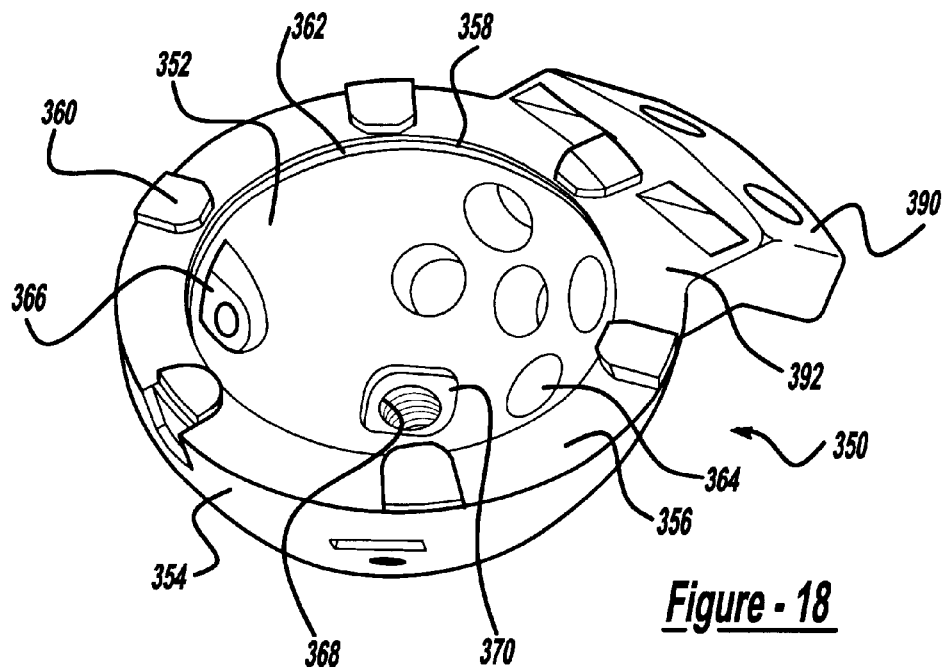
FIG. 18 is a perspective view of an acetabular cup according to the teachings of a fifth preferred embodiment of the present invention.
Figure 19:
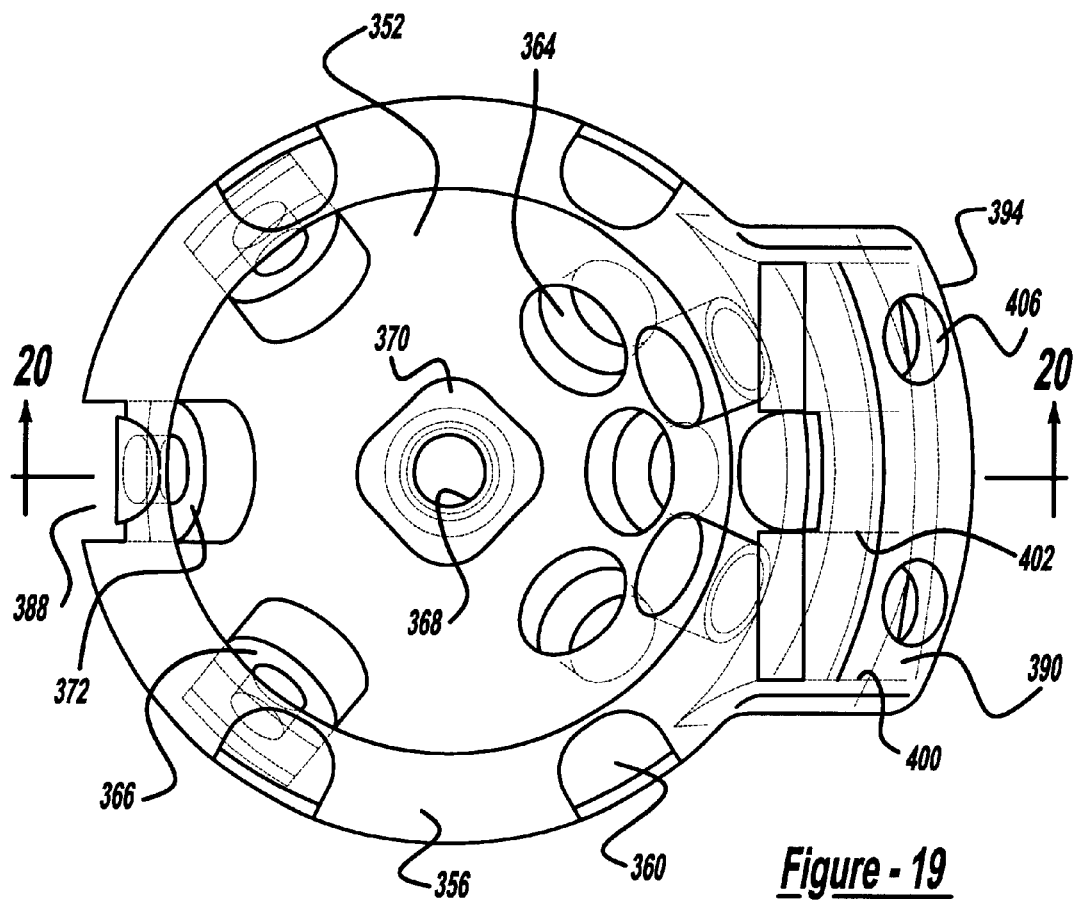
FIG. 19 is a top plane view of the acetabular cup of FIG. 18.
Figure 20:
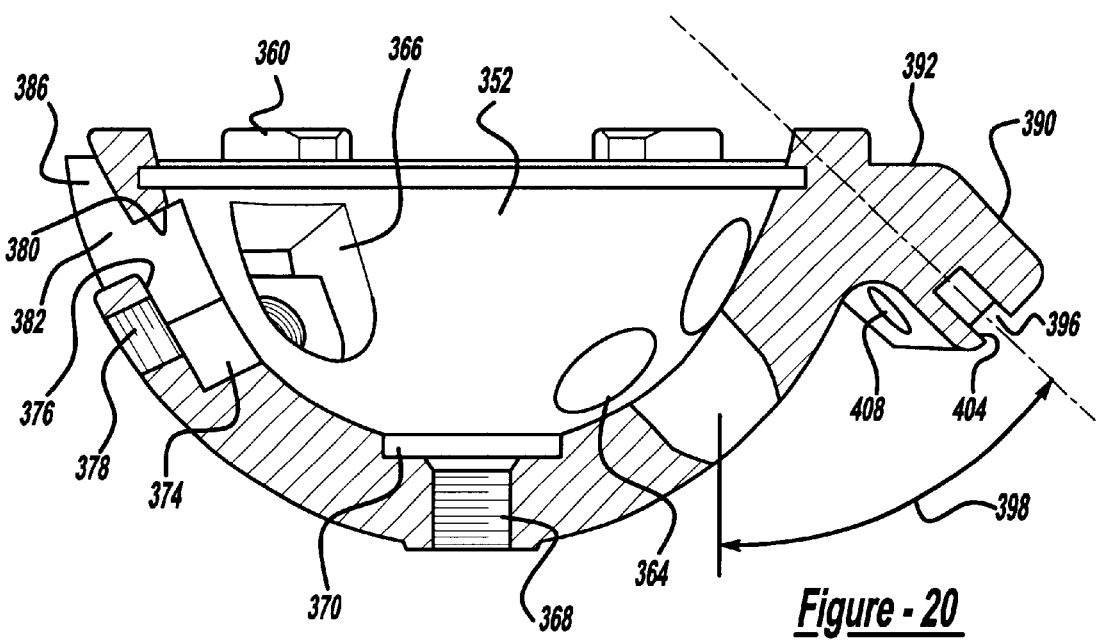
FIG. 20 is a cross-sectional view taken along line 20—20 of FIG. 19.
Figure 21:
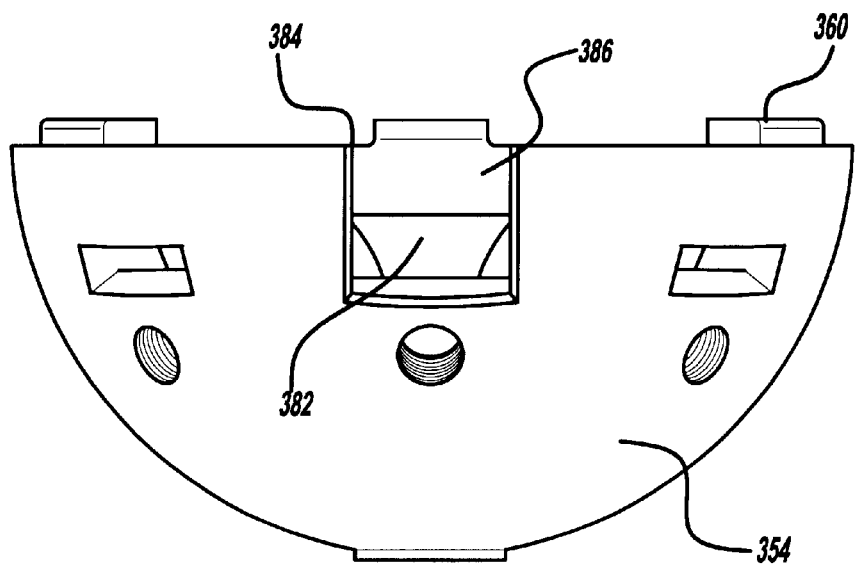
FIG. 21 is a side elevational view of the acetabular cup.

Referring to FIGS. 15 and 16, a blade guide 280 and a guide punch 282 are shown in association with the acetabular cup 12 for use in forming an arcuate bore for insertion of the ischial blade 20. The blade guide 280 is substantially spherical in shape and includes an axial centerbore 284 passing therethrough for receipt of a guide bolt 286. The blade guide 280 further includes a notched region 288 having an angled sidewall 290 that is substantially flush with the annular sidewall 30 upon inserting the blade guide 280 into the acetabular cup 12. An arcuate shaped channel 292 is defined by the blade guide 280 and includes a pair of parallel sidewall 294 and an arcuate sidewall 296. The channel 292 is aligned with the particular ischial counterbore 58 where the ischial blade 20 is to be installed.

Once aligned, the bolt 286 is passed through the bore 284 with the head 298 of the bolt 286 being nestingly received within the notch 288 as a threaded distal end 300 threadably engages the threaded bore 64. The punch 282 includes a punch body 302, a punch blade 304 and a punch handle 306. The punch blade 304 has a sharpened pointed distal end 308 and sharpened or serrated edges 310. The punch blade 304 and the body 302 have a contiguous arcuate curve 312 having the same radius as the ischial blade 20.

In use, the surgeon simply inserts and aligns the blade guide 280 within the acetabular cup 12 and secures the blade guide 280, via the bolt 286. Once the blade guide 280 is secured, the punch 282 is nestingly received within the channel 292 until a stopping face 314 of the body 302 engages the acetabular cup 12. The surgeon will simply strike the handle 306 with an appropriate impact device to drive the sharpened punch member 304 into the ischium region of the acetabulum. The punch member 304 is sized to be slightly smaller than the blade member 184 so that when the blade member 184 is implanted, it is snugly received within the ischium. It should further be noted that the ilium blade 218 may also be implanted the same way using a similar blade guide and punch having an arcuate curve that corresponds to the arcuate curve of the ilium blade 218.

The method for implanting the acetabular prosthesis 10 using the various modular attachment components will now be described with reference to FIGS. 17a–17h. It will be understood that the method for implanting the other acetabular prosthesis disclosed herein will also follow a similar procedure. It will also be understood that while the acetabular prosthesis disclosed herein, along with the modular and integral components are discussed as engaging the acetabulum or a region of the acetabulum, these components may engage just the acetabulum or any region of the acetabulum and surrounding pelvis such as the ilium, pubis and ischium or engage any other boning anatomy of a patient. Once a radiograph or x-ray has been taken of the hip or hip prosthesis that is to be replaced, a suitably sized acetabular prosthesis 10 is selected which may involve the use of a suitably sized template, as is well known in the art. Once the suitably sized acetabular prosthesis 10 is chosen, a suitably sized hip prosthesis is chosen to fit within the intramedullary canal of a host femur. The hip prosthesis may include many different types of hip prosthesis such as the Bi-Metric System, Mallory/Head System or Integral System, each available from Biomet, Inc. of Warsaw, Ind. After the suitably sized acetabular prosthesis 10 and hip prosthesis are selected, the femur or hip prosthesis is dislocated to expose the acetabulum 316 and/or a primary acetabular cup. The head of the femur in a primary surgery is then generally resected or a primary hip prosthesis is removed from the femur to provide for additional surgical clearance.

If revision surgery is performed, the primary acetabular cup is removed and the acetabulum 316 is then generally reamed with a reamer 318 driven by a driver 320. The acetabulum 316 is generally hemispherically reamed until concentric removal of all acetabular cartilage or bone cement is achieved. Once the acetabulum 316 has been appropriately reamed, acetabular trial gauges, which are well known in the art, may be used to determine and confirm the diameter of the acetabular cup 12 to be used. With the proper sized acetabular cup 12 selected, the surgeon will further decide whether or not an ilium flange 18, an ischial blade 20 or an obturator hook 22 is also required to provide appropriate securement of the acetabular cup 12 within the acetabulum 316. Should the modular ilium flange 18 and the modular obturator hook 22 be utilized, each of these components is first rigidly secured to the acetabular cup 12 with the threaded set screws 24. A conventional hex head driver is used to threadably tighten the set screws 24 to rigidly secure the ilium flange 18 and the obturator hook 22 relative to the acetabular cup 12.

Once assembled, an impacting or inserting instrument 322 is threadably inserted into the threaded centerbore 70 of the acetabular cup 12. Once the inserting instrument 322 is threadably secured to the acetabular cup 12, the inserting instrument 322 comes to rest within the rectangular counterbore 76. The inserting instrument 322 is used to properly position the acetabular cup 12 by use of multiple guide rods 324. Once the orientation of the acetabular cup 12 is acceptable, the inserting instrument 322 is solidly impacted to fully seat the acetabular cup 12, such that firm rim fixation is achieved. Once the acetabular cup 12 has been solidly impacted, the inserting instrument 322 is then carefully removed from the threaded hole 70, thereby threadably disengaging the inserting instrument 322 from the acetabular cup 12.

A plurality of bone screw holes are then bored through the holes 40 in the acetabular cup 12 using a flexible drill shaft 326 and a drill bit 328. Once fixation holes 330 have been formed in the acetabulum 316, a depth gauge, as is also known in the art, may be used to determine the length of the fixation screw. With the length of the screw determined, a fixation screw 332 or multiple screws 332 are inserted into each screw hole 330 using a universal screw driver 334. After the fixation screws 332 rigidly secure the superior region of the acetabular cup 12, a plurality of bone screw holes are now bored through the ilium region 317 of the acetabulum 316 to secure the ilium flange 18. Once the fixation holes 330 have been formed in the ilium region 317, multiple bone screws 332 are inserted into the ilium flange 18 and secured, via the universal screw driver 334. Should the ilium flange 18 need to be conformed to the ilium region 317, the ilium flange 18 may also be appropriately contoured due to the malleable nature of the ilium flange 18.

Once the ilium flange 18 has been rigidly secured to the ilium 317, the surgeon may use an adjustment instrument 336 to adjust the shape of the obturator hook 22. In this regard, the adjustment instrument 336 resembles a pair of pliers having a pair of engagement tips 337. One tip 337 engages the counterbore 46 while the other tip 337 engages the bore 172 of the obturator hook 22. Once inserted into the centerbore 46 and the bore 172, the surgeon can further contour the obturator hook 22 within the obturator foramen 338.

Once the obturator hook 22 is appropriately contoured to fit within the obturator foramen 338, the blade guide 280 is threadably secured within the acetabular cup 12, via the retaining bolt 288. Once retained, the punch 282 having the punch blade 304 is driven into the ischium 340 upon impacting the handle 306 with a mallet or appropriate impact mechanism. This forms a guide hole 342 within the ischium 340. The punch 282 is slidably removed and the blade guide 280 is removed from the acetabular cup 12 upon threadably removing the retainer bolt 286. Once the blade guide 280 and the punch 282 are removed from the acetabular cup 12, the ischial blade 20 is slidably received through the rectangular bore 68 in the acetabular cup 12 with the attachment member 179 of the ischial blade 20 being nestingly received within the ischial counterbore 58. Once seated, a set screw 24 is threadably retained within bore 178 to rigidly secure the ischial blade 20 relative to the acetabular cup 12.

With the acetabular cup 12 rigidly secured in the acetabulum 316, the acetabular cup 12 may be thoroughly cleaned and a trial liner, as known in the art, may be inserted into the acetabular cup 12. The hip prosthesis is then implanted in a manner well known in the art. With the trial liner inserted and the hip prosthesis implanted, a trial reduction can be carried out to check the full range of motion including extension, external rotation, flexion and abduction. After trial reduction, the shell liner 14 is firmly seated within the acetabular shell component 12. The shell liner 14 is appropriately seated by firmly impacting the shell liner 14 against the acetabular shell component 12. With the shell liner 14 fully seated, the ring lock 16 engages the grooves 36 and 110, thereby preventing movement of the shell liner 14 relative to the acetabular cup 12. A head 342 of the hip prosthesis 344 which is already implanted into the femur 346 is then installed in a manner known in the art into the acetabular prosthesis 10 with the head 342 bearing on the shell liner 14.

While the present method has been disclosed with respect to the modular ilium flange 18, modular ischial blade 20 and modular obturator hook 22, those skilled in the art will recognize that various other combinations can also be employed herein. In this regard, should an ilium blade be desired, an acetabular cup having a configuration to support and receive an ilium blade may be used. Should any of the particular modular attachment components not be required, a surgeon will simply not use that particular component. This configuration provides a substantially versatile system enabling a surgeon to meet several patient configurations.

Turning to FIGS. 18–21, a full-hemisphere acetabular cup 350 according to the teachings of a fifth preferred embodiment of the present invention is shown. The acetabular cup 350 is substantially similar to the acetabular cup 12 except for some additional variations, further discussed herein. The acetabular cup 350 includes a smooth inner concave surface 352, a roughened or porous coated outer surface 354, an annular face 356 having a shoulder 358 and a plurality of arcuate alignment tabs 360. Positioned adjacent to the shoulder 358 is an annular groove 362 that receives the ring lock 16 to secure the bearing liner 14 in the concave surface 352 of the acetabular cup 350. The acetabular cup 350 also includes a plurality of bone screw holes 364 that are defined by the acetabular cup 350 and located in the superior region similar to the acetabular cup 12. Positioned inferior to the bone screw holes 364 are right and left ischial counterbores 366 shaped substantially the same as the counterbores 58 in the acetabular cup 12. Passing centrally through the acetabular cup 350 is a threaded bore 368 having a substantially square counterbore 370, also similar to that shown in the acetabular cup 12.

Located also inferiorly to the bone screw holes 364 is an anti-rotation obturator counterbore 372, also defined by the acetabular cup 350. The obturator counterbore 372 is different from the obturator counterbore 46 in the acetabular cup 12. In this regard, the obturator counterbore 372 resembles the obturator counterbore 46 from the inner concave surface 352, but is shaped differently at the outer convex surface 354. Specifically, the obturator counterbore 372 includes the D-shaped sidewall 374 having the stepped shoulder 376 (see FIG. 20). Passing through the stepped shoulder is a threaded bore 378 which is operable to threadably receive one of the threaded set screws 24. A rectangular shaped sidewall 380 extends from the concave surface 352 outward to the convex surface 354 to define a rectangular bore 382. The outer convex surface 354 further includes or defines an outer rectangular sidewall 384 that forms an outer counterbore 386 opposite the obturator counterbore 372. A clearance notch 388 is also formed in the annular rim 356 to provide for clearance of an obturator hook, further discussed herein.

Extending from the annular surface 356 and located in the superior region is an angled attachment plate 390. The attachment plate 390 includes a planar face 392 which extends substantially planar with the annular surface 356. The attachment plate 390 further includes a convex surface 394 and is operable to receive an ilium flange, further discussed herein. Passing through the face 392 and the sidewall 394 is an angled channel 396 that has an angle of about 45° relative to the annular surface 356, identified by reference numeral 398. The channel 396 is defined by inner parallel sidewalls 400 and an internal key 402. The channel 396 further includes a pair of parallel top and bottom sidewalls 404. Passing transversely through the attachment plate 390 are a pair of counterbores 406 and threaded bores 408.

Figure 22:
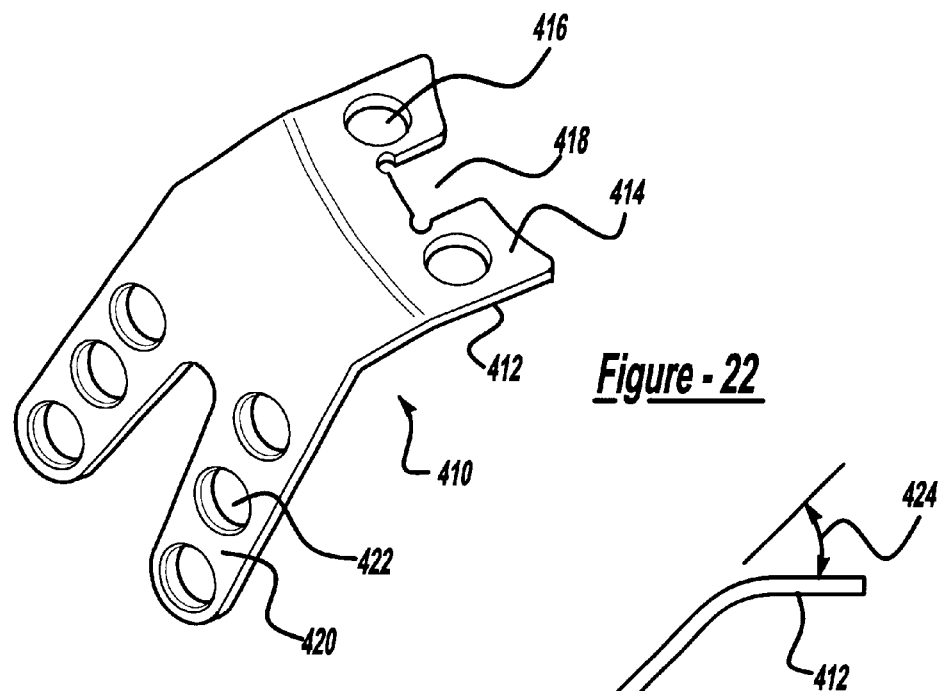
FIG. 22 is a perspective view of a large right ilium flange according to the teachings of the fifth preferred embodiment of the present invention.
Figure 23:
FIG. 23 is a side view of the ilium flange of FIG. 22.
Figure 24:
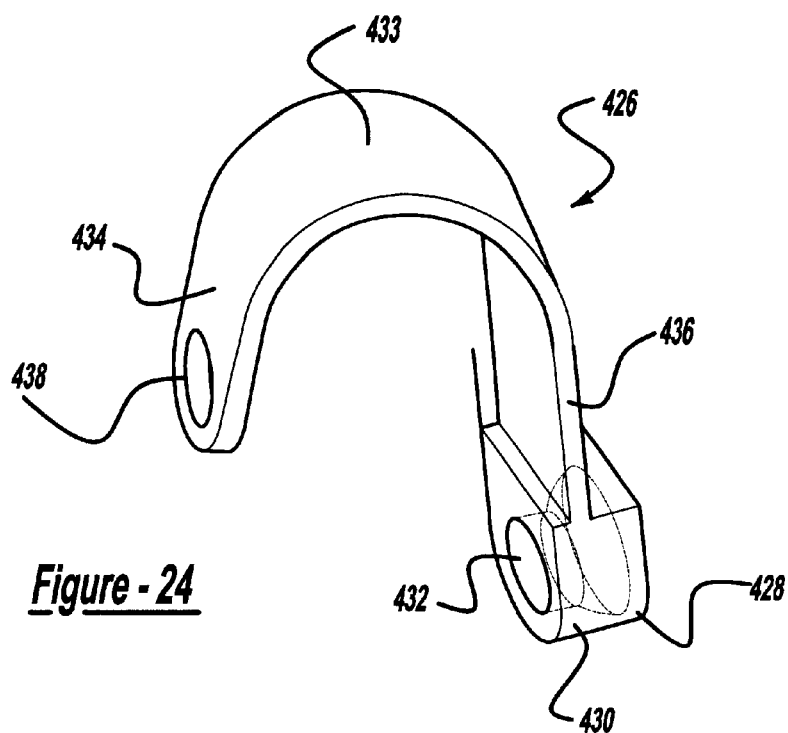
FIG. 24 is a perspective view of an obturator hook according to the teachings of the fifth preferred embodiment of the present invention.

Referring to FIGS. 22 and 23, a large right ilium flange 410 is shown which is slidable received within the channel 396 of the acetabular cup 350. It should first be noted that while a large right ilium flange 410 is shown, it is to be understood that various other size flanges having sizes similar to those shown in FIGS. 8A–8D, as well as left ilium flanges will also be provided. The ilium flange 410 is substantially similar to the ilium flange 18 in that it includes an attachment member 412 that includes a pair of wings 414 that are slidably and nestingly received within the channel 396. Each wing 414 includes a bore 416 and defines a notch region 418 that nestingly mates about the internal key 402. Upon the notch region 418 nestingly engaging the key 402, the bores 414 are positioned substantially concentric with the bores 406 and 408, whereby the set screws 24 may be used to retain the ilium flange 410 relative to the acetabular cup 350. Here again, this two-point contact provides a substantially rigid connection between the modular ilium flange 410 and the acetabular cup 350, thereby substantially inhibiting the rotational or micro-motion between the flange 410 and the acetabular cup 350.

The ilium flange 410 also includes a pair of angled fingers 420 each defining a plurality of bone screw holes 422. The pair of fingers 420 are angled from the attachment member 412 by an angle of about 45°, identified by reference numeral 424. Since the attachment plate 390 is angled relative to the annular surface 356, the ilium flange 410 does not require the configuration, as shown in FIGS. 8A–8D. In this regard, the angled attachment plate 390 provides a closer conformity of the ilium flange 410 relative to the ilium region 317.

An obturator hook 426 is shown in FIG. 23, that rigidly mates with the acetabular cup 350. The obturator hook 426 includes an attachment member 428 having a substantially D-shaped sidewall 430 which mates with the obturator counterbore 374. The attachment member 428 further defines a bore 432 which substantially aligns with the bore 378 for rigidly attaching the obturator hook 426 to the acetabular cup 350. The obturator hook 426 further includes a substantially arcuate engagement member 433 having a distal end 434 which is substantially parallel with a proximal end 436. Passing through the distal end 434 is a bore 438 which is operable to receive a bone screw or may be used for further shaping of the obturator hook 426. The obturator hook 426 is preferably formed from commercially pure titanium or any other biocompatible material which is preferably malleable.

Figure 25:
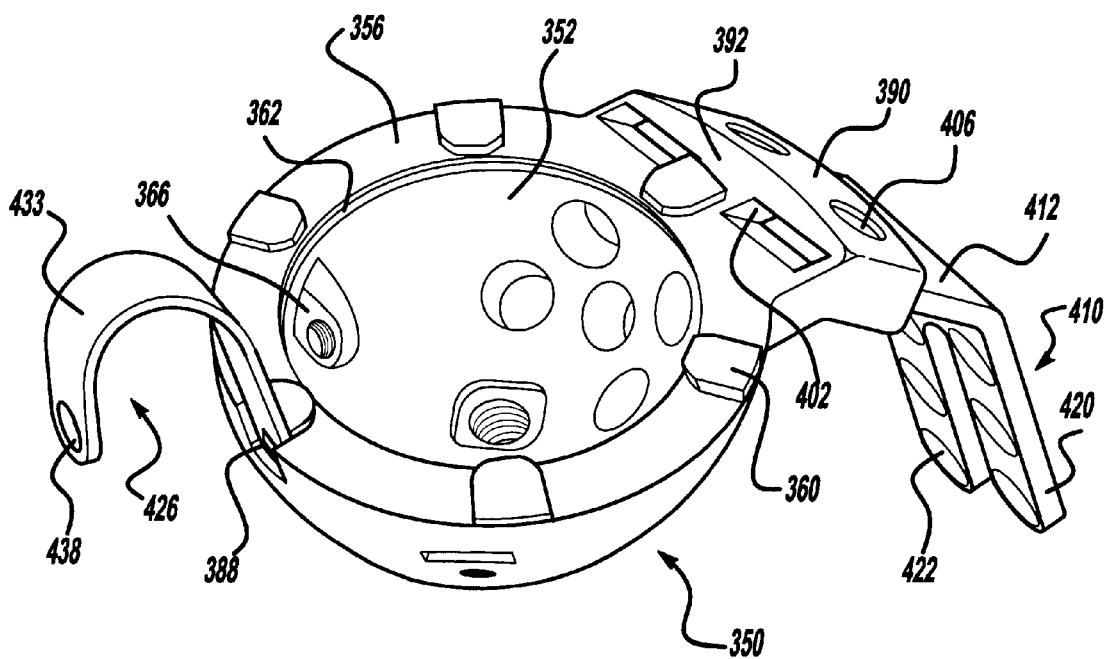
FIG. 25 is a perspective view of the assembled acetabular prosthesis according to the teachings of the fifth preferred embodiment of the present invention.

Finally, referring to FIG. 25, the acetabular cup 350 is shown assembled with the ilium flange 410 and the obturator hook 426. In this regard, the ilium flange 410 angles immediately downward from the acetabular cup 350 to place the ilium flange 410 substantially adjacent to the ilium region 317. The obturator hook 426 is attached to the acetabular cup 350 by way of slidably passing the attachment member 428 through the notch region 388 until the attachment member 428 slidably rests within the obturator counterbore 372. By providing the clearance notch 388, the proximal end 436 of the engagement member 432 is able to extend upward from the annular surface 356 as compared to the obturator hook 422, shown in FIG. 9, which extends below the annular surface 356. This provides further versatility in affixation of the acetabular cup 350 relative to the acetabulum 316. The acetabulum 350 is also implanted substantially similar to that set forth in FIGS. 17A–17H.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An acetabular prosthesis for implantation in an acetabulum and surrounding pelvis, said acetabular prosthesis comprising:

an acetabular cup having an outer surface operable to be received in the acetabulum and an inner surface operable to receive a bearing liner;

an anti-rotation counterbore defined by said inner surface of said acetabular cup, said anti-rotation counterbore is formed by a sidewall extending along said inner surface of said acetabular cup and includes at least one bore located within said anti-rotation counterbore and passing through said acetabular cup; and a modular attachment component having an attachment member and an engagement member, said attachment member operable to substantially nest within said anti-rotation counterbore and said engagement member operable to engage a region of the acetabulum, wherein upon positioning said attachment member in said anti-rotation counterbore, said modular attachment component is inhibited from rotational movement relative to said acetabular cup.

2. The acetabular prosthesis as defined in claim 1, wherein said engagement member is operable to engage a region selected from the group consisting of the acetabulum, the ischium region of the acetabulum, the ilium region of the acetabulum and the pubis region of the acetabulum.

3. The acetabular prosthesis as defined in claim 1 wherein said attachment member has a sidewall that is substantially congruent to said sidewall of said anti-rotation counterbore and said engagement member passes through said at least one bore.

4. The acetabular prosthesis as defined in claim 1 wherein said anti-rotation counterbore includes at least two bores passing through said acetabular cup, each of said bores being substantially rectangular and parallel to one another.

5. The acetabular prosthesis as defined in claim 1 wherein said sidewall includes at least one corner.

6. The acetabular prosthesis as defined in claim 5 wherein said sidewall has a D-shape.

7. The acetabular prosthesis as defined in claim 1 wherein said anti-rotation counterbore is further formed by a sidewall extending along said outer surface that defines a clearance notch within an annular surface between said inner and outer surfaces.

8. The acetabular prosthesis as defined in claim 1 wherein said modular attachment component is selected from a group consisting of an ilium flange, an ischium blade and an obturator hook.

9. The acetabular prosthesis as defined in claim 8 wherein each of said modular attachment components is operable to be secured to said acetabular prosthesis by way of a threaded set screw.

10. The acetabular prosthesis as defined in claim 1 wherein said engagement member is an elongated blade.

11. The acetabular prosthesis as defined in claim 1 wherein said engagement member is an obturator hook having a bore passing therethrough, said bore operable to be engaged by an adjustment bar to conform a shape of said obturator hook to an obturator foramen.

12. An acetabular prosthesis for implantation in an acetabulum and surrounding pelvis, said acetabular prosthesis comprising:

an acetabular cup having an outer surface operable to be received in the acetabulum, an inner surface operable to receive a bearing liner, and an annular region extending between said outer surface and said inner surface;

an attachment plate extending from said annular region, said attachment plate defining an internal channel having an internal key positioned within said internal channel; and a modular attachment component having an attachment member and an engagement member, said attachment member operable to be slidably received within said channel and positioned about said internal key and said engagement member operable to engage a region of the acetabulum, wherein upon said attachment member being slidably received in said channel, said modular attachment component is inhibited from rotational movement relative to said acetabular cup.

13. The acetabular prosthesis as defined in claim 1 wherein said engagement member is operable to engage a region selected from the group consisting of the acetabulum, the ischium region of the acetabulum, the ilium region of the acetabulum and the pubis region of the acetabulum.

14. The acetabular prosthesis as defined in claim 12 wherein said attachment member includes a pair of wing members and a notch region operable to be slidably positioned about said internal key.

15. The acetabular prosthesis as defined in claim 12 wherein said modular attachment component is secured to said attachment plate by at least two securement points.

16. The acetabular prosthesis as defined in claim 15 wherein said modular attachment component is secured to said attachment plate by at least two set screws.

17. The acetabular prosthesis as defined in claim 12 wherein said modular attachment component is a modular ilium flange defining a plurality of holes operable to receive a plurality of bone screws.

18. The acetabular prosthesis as defined in claim 12 wherein said attachment plate angles downward from said annular region whereby said internal channel is angled relative to said annular region.

19. The acetabular prosthesis as defined in claim 12 further comprising a second modular attachment component selected from the group consisting of an ilium flange, an ischium blade, and an obturator hook.

20. An acetabular prosthesis for implantation in an acetabulum and surrounding pelvis, said acetabular prosthesis comprising:

an acetabular cup having an outer surface operable to be received in the acetabulum and an inner surface operable to receive a bearing liner;

an anti-rotation counterbore defined by said inner surface of said acetabular cup and formed by a recessed sidewall extending from said inner surface;

at least one slot defined by said acetabular cup and passing through said acetabular cup from said inner surface to said outer surface, said at least one slot located within said anti-rotation counterbore; and a modular attachment component having an attachment member and an elongated blade, said attachment member operable for use in attaching said modular attachment component to said acetabular cup and said elongated blade operable to pass through said at least one slot to provide intramedullary fixation of said acetabular cup in a region about the acetabulum.

21. The acetabular prosthesis as defined in claim 20 wherein said elongated blade is operable to provide intramedullary fixation in the regions selected from the group consisting of the acetabulum, the ischium region of the acetabulum, the ilium region of the acetabulum and the pubis region of the acetabulum.

22. The acetabular prosthesis as defined in claim 20 wherein said elongated blade has an elongated arcuate shape.

23. The acetabular prosthesis as defined in claim 22 wherein said elongated blade has an arcuate cross section.

24. The acetabular prosthesis as defined in claim 20 wherein said attachment member has a sidewall that substantially nests within said counterbore formed about said at least one slot.

25. A method for implanting an acetabular prosthesis having a modular attachment component in an acetabulum and surrounding pelvis, said method comprising:

providing an acetabular cup having an outer surface operable to be received in the acetabulum and an inner surface operable to receive a bearing liner;

engaging the outer surface of the acetabular cup with a surgically prepared portion of the acetabulum;

locating a punch guide along the inside surface of the acetabular cup;

guiding a punch through said acetabular cup and into the acetabulum with the punch guide to form a hole in the acetabulum;

removing the punch and punch guide from the acetabular cup;

passing a portion of the modular attachment component through the acetabular cup and into the hole formed by the punch; and securing the modular attachment component to the acetabular cup within an anti-rotation counterbore formed by a sidewall extending along said inner surface of said acetabular cup and includes at least one bore located within said anti-rotation counterbore and passing through said acetabular cup.

26. The method as defined in claim 25 further comprising passing a blade portion of the modular attachment component through the acetabular cup and into the hole formed by the punch.

* * * * *